US008679062B2

(12) United States Patent
Yodfat et al.

(10) Patent No.: US 8,679,062 B2
(45) Date of Patent: Mar. 25, 2014

(54) APPARATUS AND METHOD FOR PUMPING FLUID

(75) Inventors: Ofer Yodfat, Maccabim-Reut (IL); Ofer Arnold, Menashe' (IL); Avraham Neta, Misgav (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 335 days.

(21) Appl. No.: 12/082,295

(22) Filed: Apr. 10, 2008

(65) Prior Publication Data

US 2008/0255516 A1    Oct. 16, 2008

Related U.S. Application Data

(60) Provisional application No. 60/922,794, filed on Apr. 10, 2007.

(51) Int. Cl.
*A61M 1/00* (2006.01)
*A61M 37/00* (2006.01)

(52) U.S. Cl.
USPC .......................................... 604/153; 604/131

(58) Field of Classification Search
USPC .............. 604/131, 151–154, 174, 180, 890.1
See application file for complete search history.

(56) References Cited

U.S. PATENT DOCUMENTS

| 3,631,847 | A |   | 1/1972 | Hobbs | 128/2 R |
| 3,771,694 | A |   | 11/1973 | Kaminski | 222/70 |
| 4,236,880 | A | * | 12/1980 | Archibald | 417/478 |
| 4,498,843 | A |   | 2/1985 | Schneider et al. | 417/22 |
| 4,544,369 | A |   | 10/1985 | Skakoon et al. | 604/155 |
| 4,657,486 | A |   | 4/1987 | Stempfle et al. | 417/12 |
| 5,330,431 | A | * | 7/1994 | Herskowitz | 604/153 |
| 5,848,990 | A |   | 12/1998 | Cirelli et al. | 604/136 |
| 5,957,895 | A |   | 9/1999 | Sage et al. | 604/181 |
| 5,984,894 | A |   | 11/1999 | Poulsen et al. |  |
| 6,203,296 | B1 | * | 3/2001 | Ray et al. | 417/477.7 |
| 6,423,035 | B1 | * | 7/2002 | Das et al. | 604/155 |
| 6,485,461 | B1 |   | 11/2002 | Mason et al. | 604/132 |
| 6,589,229 | B1 |   | 7/2003 | Connelly et al. | 604/890.1 |

(Continued)

FOREIGN PATENT DOCUMENTS

| CA | 2 170 237 | 3/1995 |
| EP | 0 272 530 | 12/1987 |

(Continued)

OTHER PUBLICATIONS

International Search Report dated Apr. 25, 2008 for PCT/IL2007/001454.

(Continued)

*Primary Examiner* — Jason Flick
*Assistant Examiner* — Jenna Zhang
(74) *Attorney, Agent, or Firm* — Mintz Levin Cohn Ferris Glovsky and Popeo, P.C.

(57) ABSTRACT

Methods, systems, and apparatuses for delivering therapeutic fluid to a user are disclosed. The apparatus includes a pump mechanism for pumping therapeutic fluid to the user having a reusable part which includes a housing and a disposable part configured to be inserted into the housing of the reusable part and to be connected with the reusable part. The connection of the reusable part and the disposable part enables operation of the pump mechanism and disconnection of the reusable part and the disposable part disables operation of the pump mechanism.

30 Claims, 34 Drawing Sheets

(56) References Cited

U.S. PATENT DOCUMENTS

| | | |
|---|---|---|
| 6,669,668 B1 * | 12/2003 | Kleeman et al. ............... 604/131 |
| 6,699,218 B2 | 3/2004 | Flaherty et al. ............... 604/131 |
| 6,723,072 B2 | 4/2004 | Flaherty et al. ............... 604/131 |
| 6,740,059 B2 | 5/2004 | Flaherty ........................... 604/67 |
| 2002/0169439 A1 | 11/2002 | Flaherty |
| 2003/0032935 A1 | 2/2003 | Damiano et al. ............... 604/403 |
| 2004/0133164 A1 | 7/2004 | Funderburk et al. ........... 604/134 |
| 2004/0158207 A1 | 8/2004 | Hunn et al. ............... 604/164.01 |
| 2004/0162521 A1 | 8/2004 | Bengtsson ..................... 604/136 |
| 2004/0204673 A1 * | 10/2004 | Flaherty ........................... 604/65 |
| 2005/0101912 A1 | 5/2005 | Faust et al. .................... 604/117 |
| 2007/0191702 A1 | 8/2007 | Yodfat et al. .................. 600/365 |
| 2008/0214916 A1 | 9/2008 | Yodfat et al. .................. 600/347 |
| 2008/0215035 A1 | 9/2008 | Yodfat et al. .................. 604/513 |

FOREIGN PATENT DOCUMENTS

| | | |
|---|---|---|
| EP | 1 464 351 | 1/1999 |
| EP | 1 384 490 | 1/2004 |
| EP | 1527792 A1 * | 5/2005 |
| EP | 1 731 128 | 12/2006 |
| FR | 2 753 236 A | 3/1998 |
| GB | 2 414 398 | 11/2005 |
| WO | WO 00/35517 | 6/2000 |
| WO | WO 03/090509 | 11/2003 |
| WO | WO 2004/024211 | 3/2004 |
| WO | WO 2004/030726 | 4/2004 |
| WO | WO 2005/065748 | 7/2005 |
| WO | WO 2005/074860 | 8/2005 |
| WO | WO 2005/112800 | 12/2005 |
| WO | WO 2006/015301 | 2/2006 |
| WO | WO 2006/015600 | 2/2006 |
| WO | WO 2006/061354 | 6/2006 |
| WO | WO 2006/108809 | 10/2006 |
| WO | WO 2007/015233 | 2/2007 |
| WO | WO 2008/012817 | 1/2008 |
| WO | WO 2008/020447 | 2/2008 |
| WO | WO 2008/053368 | 5/2008 |
| WO | WO 2008/065646 | 6/2008 |

OTHER PUBLICATIONS

International Search Report dated Dec. 21, 2007 for PCT/IL2007/001027.

International Search Report dated Nov. 19, 2007 for PCT/IL2007/000932.

International Search Report, PCT Application No. PCT/IL2008/000499, date of mailing Aug. 21, 2008.

* cited by examiner

APPARATUS AND METHOD FOR PUMPING FLUID

CROSS-REFERENCE TO RELATED APPLICATIONS

The present application claims priority to U.S. Provisional Patent Application Ser. No. 60/922,794, filed Apr. 10, 2007, and entitled "Apparatus and Method for Pumping Fluid Into A Mammal's Body", the disclosure of which is incorporated herein by reference in its entirety.

FIELD OF THE INVENTION

Embodiments of the present invention generally relate to systems, devices and methods for pumping of fluids into a body and, particularly, to a portable pump (for example, a patch) that can be coupled or adhered to the skin of a patient. The fluid pumping device is provided with a pump mechanism deployed within a housing having two relatively displaceable parts. The pump mechanism can be enabled or disabled upon displacement of the housing parts.

BACKGROUND OF INVENTION

Medical treatment of several illnesses requires continuous drug infusion into various body compartments, such as subcutaneous and intra-venous injections. For example, diabetes mellitus patients require the administration of varying amounts of insulin throughout the day to control their blood glucose levels. In recent years, ambulatory portable insulin infusion pumps have emerged as superior alternatives to multiple daily injections of insulin using a syringe. These pumps, which deliver insulin at continuous basal rates, as well as, in bolus volumes, were developed to liberate patients from repeated self-administered injections, and allow them to maintain a near-normal daily routine. Both basal and bolus volumes must be delivered in precise doses, according to individual prescription, since an overdose of insulin could be fatal. Therefore, insulin injection pumps must feature high reliability, preventing delivery of any unintentional insulin excess.

Several ambulatory insulin infusion pumps are currently available on the market. Mostly, these devices have two parts: a durable portion, containing a dispensing means, a controller and electronics, and a disposable portion containing a reservoir for insulin, a needle assembly (cannula and penetrating member), and a fluid delivery tube altogether named "infusion set". Usually, the patient fills the reservoir, attaches the infusion set to the exit port of the reservoir, and then inserts the reservoir into the pump housing.

After purging air out of the reservoir, the delivery tube and the needle, the patient inserts the needle assembly, at a selected location on the body, and then upon subcutaneous insertion of the needle of the penetrating member, withdraws the penetrating member, while leaving the cannula inserted. To avoid irritation and infection, the subcutaneous cannula must be replaced and discarded after two to three days, together with the empty reservoir.

Examples of a first generation disposable syringe-type reservoir and tubes were disclosed in U.S. Pat. No. 3,631,847 to Hobbs, U.S. Pat. No. 3,771,694 to Kaminski, and later U.S. Pat. No. 4,657,486 to Julius, and U.S. Pat. No. 4,544,369 to Skakoon. The driving mechanism of the dispensing means of these devices is a screw thread plunger, which controls the programmed movement of a syringe piston. These devices represent a significant improvement over multiple daily injections, but all suffer from several drawbacks. The main drawbacks are their large sizes and weight of the devices, which are a result of their spatial configurations and relatively large driving mechanisms of the syringe and piston. The relatively bulky device had to be carried in a patient's pocket or attached to the belt. Consequently, the fluid delivery tube was long, usually longer than 60 cm, in order to allow needle insertion in remote sites of the body. These uncomfortable bulky devices with a long tube were rejected by the majority of diabetic insulin users because they disturb regular activities, such as sport activities and swimming. Furthermore, the effect of the image projected on a teenager's body is unacceptable. In addition, the fluid delivery tube excludes some optional remote insertion sites, like the buttocks and the extremities. To avoid the tubing limitations, a new concept of a second generation was proposed.

This new concept related to a skin adherable device with a housing having a bottom surface adapted for contact with the patient's skin, a reservoir contained within the housing, and an injection needle adapted for communication with the reservoir. This skin adherable device was designed to be disposed every 2-3 days similarly to the currently available pump infusion sets.

This design was disclosed in U.S. Pat. No. 4,498,843 to Schneider, U.S. Pat. No. 5,957,895 to Burton, U.S. Pat. No. 6,589,229 to Connelly, and U.S. Pat. No. 6,740,059 to Flaherty. Additional configurations of conventional skin adherable pumps are disclosed in U.S. Pat. Nos. 6,723,072 and 6,485,461.

In these patents, the pump includes one piece and has to be adhered to the patient's skin for the entire usage duration while the needle that emerges from the bottom surface of the device is being fixed to the device housing.

These second-generation skin adherable devices have several limitations:

They waste insulin—a single-piece device must be disposed after each pump replacement (i.e., every 2-3 days) including unused insulin. Further, in cases of site misplacement (scar tissue, bleeding, cannula kinking, etc.), the entire device including fully filled insulin reservoir must be disposed.

They are expensive—the entire device including relatively expensive parts must be disposed after each pump replacement. Thus, the production cost is high and the final product price far exceeds Medicare allowable payments.

They are bulky and heavy—the automatic insertion mechanism employed in these devices occupies substantial volume, as disclosed in for example, U.S. Pat. No. 6,699, 218. Thus, although the insertion process ends, the patient must carry the heavy and bulky insertion mechanism (springs, etc.) for the entire usage duration.

An attempt to eliminate these drawbacks included a two-piece conventional skin adherable dispensing patch unit having two parts:

A reusable part—a first housing that contains the driving and pumping mechanism, electronics and other relatively expensive components.

A disposable part—a second housing that contains components such as reservoir, tubes and batteries, that can last until reservoir is emptied, i.e., usually a few days.

This concept provides a cost-effective device and allows diverse usage of the device, e.g., the use of various reservoir sizes, various needle and cannula types and effecting of versatile operational modes. There are various applicable types of pumping mechanisms for the two-piece device configuration.

Conventional delivery mechanisms include linear positive displacement pumping mechanism having a rotary wheel with rollers, a stator and a resilient delivery tube. The tube is located between the rotary wheel and the stator.

While the rotary wheel rotates, the rollers continuously "squeeze" the tube in one direction only, displacing the fluid within the tube from the reservoir towards the exit port provided at the housing. The stator is biased by a spring and is pressed towards the delivery tube against the rotary wheel, preventing coarse movements of the tube.

The conventional delivery mechanism devices suffer from several limitations:

The devices are expensive—each part (disposable and/or reusable) is enclosed within a different housing. Since the disposable part should be often replaced e.g., every 3 days, its housing becomes a major cost factor. Additional cost increase occurs when the stator is configured to be a part of the disposable part.

Sealing hurdles—it is very difficult to manufacture the two parts with a perfect connection due to tolerances and inaccuracies of assembly causing imperfect sealing in parts' connection.

Fluid delivery inaccuracies—delivery tube, rotary wheel and stator are not necessarily located in the same part of the dispensing patch unit (e.g., the stator and the delivery tube are located in the disposable part, while the rotary wheel is located in the reusable part). When connecting the disposable and reusable parts together, the matching of these three components may be mechanically imperfect due to manufacturing tolerances and inaccuracy of assembly. This can cause inaccurate fluid delivery.

The devices are not safe—an initial connection of the reusable part and the disposable part is done by the patient and not in the factory. Therefore a fault connection may happen leading to drug over- or under-dosing.

Status of reservoir content—since the reservoir is located within the disposable housing, the patient is not aware of fluid status in the reservoir during the priming procedure, i.e., while filling the reservoir, the patient is not aware of the current amount of fluid disposed within the reservoir.

Another drawback of existing skin adherable drug infusion devices is associated with the process of insertion. In cases of fault insertions, the whole device must be discarded including the fluid within (i.e., pre-used insulin). This process is cumbersome and costly, In view of the foregoing, it would be desirable to provide improved systems, methods, and devices for sustained medical infusion of fluids.

SUMMARY OF THE INVENTION

Embodiments of the present invention provide improved systems, methods, and for sustained medical infusion of fluids.

In some embodiments, a fluid delivery device is provided with a configuration that provides separation between the infusion device and the drug delivery mechanism (i.e., needle, cannula, array of micro-needles).

In some embodiments, a fluid delivery device is provided that is configured as a miniature portable programmable fluid dispensing patch unit that has short external tubing or substantially no external tubing, and that can be adhered to the body at any desired location. As used herein, the fluid dispensing patch unit sometimes will be referred to as a dispensing patch or dispensing unit. As can be understood by one skilled in the art, such reference is provided here for exemplary, non-limiting purposes.

In some embodiments, a fluid delivery device includes a dispensing patch unit and a carrier unit, which can be adhered to the skin. The dispensing patch unit can be connected to the carrier unit. The carrier unit retains the dispensing patch unit attached to the body without directed adherence.

In some embodiments, a fluid delivery device includes a dispensing patch unit that can be disconnected from and reconnected to the patient, thereby allowing temporary removal of the device, in such cases as taking hot bath, sauna, intimacy, etc. Based on the configuration of the device, disconnections and reconnections do not harm various components of the patch (e.g., pumping mechanism and needle), the surrounding tissue and/or the patient.

In some embodiments, the present invention's device includes a dispensing patch unit and a cradle unit, where the cradle unit is adherable to the skin, and where the dispensing patch unit can be connected to and disconnected from the cradle unit upon patient's discretion.

In some embodiments, the fluid delivery device has a dispensing patch unit that can be programmed by a remote control unit and/or by buttons provided on the dispensing patch.

In some embodiments, the present invention's device contains a dispensing patch unit that has two parts: a disposable part and a reusable part. In these embodiments, relatively expensive components can be disposed within the reusable part (e.g., electronic, driving mechanism, transceiver, etc.) and relatively inexpensive components can be disposed within the disposable part (e.g., reservoir, batteries etc.).

In some embodiments, the present invention's device includes a dispensing patch unit that has two parts, which after connection allow the unified device to have a thin profile.

In some embodiments, the device includes a dispensing patch having two parts: a reusable part and a disposable part. After connection of the two parts, the unified device allows the pumping mechanism, located in the reusable part, to dispense fluid from the reservoir, located in the disposable part.

In some embodiments, the device includes a dispensing patch unit that having two parts and allows accurate, safe and user-friendly connection of the two parts.

In some embodiments, the fluid delivery device includes a dispensing patch unit and a carrier unit. The carrier unit is adherable to the skin and allows connection of a two-part dispensing patch unit to the body. The carrier unit retains the connection of the two parts using a peripheral support, thus, enabling effective sealing between them.

In some embodiments, the device includes a dispensing patch unit having two parts: a reusable part and a disposable part. The reusable part contains a linear positive displacement pumping mechanism including rotating wheel and a stator. After connection of the two parts, the pumping mechanism allows fluid dispensing from the reservoir disposed in the disposable part.

In some embodiments, the device includes a dispensing patch unit having a reservoir that allows simple filling of the reservoir and during filling, the user is able to observe the fluid disposed within the reservoir. In some embodiments, the filling of the reservoir may be carried out by a dedicated adapter.

In some embodiments, the device includes a dispensing patch unit having two parts: a reusable part and a disposable part, where the battery is disposed within the disposable part. Thus, this avoids patient involvement in handling and replacement of the battery.

In some embodiments, the dispensing patch unit includes two parts: a reusable part and a disposable part, where the seal between the parts, subsequent to their connection, is complete and does not affect the device's function.

In some embodiments, the device includes a dispensing patch unit that allows manual needle insertion or automatic needle insertion using the aim of a dedicated inserter.

Some embodiments of the present invention relate to a fluid delivery device that includes a dispensing patch unit that can be adhered to the skin of a patient and that delivers therapeutic fluid to the body. In the following description, this unit can sometimes be referred to as: skin adherable dispensing patch unit, dispensing patch, infusion patch, dispensing unit, patch unit or interchangeable dispenser.

Some embodiments of the invention are implemented as a miniature portable programmable fluid dispenser. The dispenser may be adhered to the skin at any desired location. Fluid flow instructions can be programmed manually by pushing buttons located on the patch or be remotely transmitted to the dispensing patch unit by the remote control unit. In some embodiments, the dispenser is a single unit having two parts: a reusable part and a disposable part. The dispenser can be adhered directly to the skin, using a dedicated carrier unit, or using a cradle unit.

In some embodiments, the dispensing patch unit includes a reservoir, a driving mechanism which may include for example an electrical DC, a stepper motor, a shape memory alloy actuator, or the like, and a pumping mechanism, such as a peristaltic pump, a syringe/piston pump, or the like. The dispensing patch unit may also include a power supply and electronics. In some embodiments, the dispensing patch unit employs a linear positive displacing pump composed of a rotary wheel and rollers that squeeze a delivery tube against a stator displacing fluid from a reservoir towards the body. The connection of the two parts is done by inserting the disposable part into the reusable part. Closing the reusable part over the disposable part with a cover may establish electrical connections and a power supply for energizing electronic components and the rotary wheel. In addition, the rotary wheel may be coupled to the stator that squeezes the delivery tube against the rotary wheel allowing fluid pumping.

Fluid delivery into the subcutaneous compartment may be done using a soft cannula. The cannula may be inserted either manually or by using a dedicated inserter followed by penetrating member withdrawal.

In some embodiments, communication between the patch unit and the cannula within the subcutaneous compartment can be performed as follows:
  Directly connecting cannula to a patch unit's exit port;
  Connecting infusion set (a short tube) to the patch unit either directly or via a luer;
  Penetrating, via a well portion, a fluid collection element and the skin of the patient using a cannula.
  Separating the cradle unit that contains cradle and cannula. The user can connect and disconnect the dispensing patch unit from the cradle unit. A short connecting lumen (located in the dispensing patch unit) pierces a self sealed septum (e.g., rubber septum located in the cradle unit).

In some embodiments, the device can include one or more of the following units and parts:
1. A dispensing patch unit containing the driving and pumping mechanisms, a reservoir, a delivery tube and an exit port. In some embodiments, the dispensing patch unit includes two parts as follows:
   i. A reusable part—containing components that can be used many times, such as, the driving and pumping mechanisms.
   ii. A disposable part—containing disposable components that can be used until emptying the reservoir, such as, the reservoir, the delivery tube, the exit port. It may contain also a flat sheet with an adhesive layer facing the skin and a connecting means to allow connection of the dispensing patch unit to a cradle unit.
2. A cradle unit, containing the following parts:
   i. A cradle part, which is configured as a resilient sheet. Its bottom is coated with an adhesive to enable adherence to the skin. Its upper side includes connecting means for connection to and disconnection from the dispensing unit.
   ii. A cannula and a penetrating member. The penetrating member is removed after insertion. The cannula and the penetrating member may be subcutaneously inserted either manually or with the aid of an inserter. Cannula can be inserted manually or using an inserter as follows:
      1. Externally to the dispensing unit—a short external tube connecting the cannula and the exit port of the dispensing patch unit;
      2. Through a well portion; or,
      3. Using a component of the cradle part.
   iii. A well portion.
3. A carrier unit that includes:
   i. A skin adherable frame having a bottom portion that may be coated with an adhesive that enables carrying of the dispensing patch unit.
4. A remote control unit for programming flow and data acquisition.

In some embodiments, methods, systems and devices disclosed herein may be used for medical infusion of therapeutic fluids into the body.

In some embodiments, a device is provided for sustained medical infusion with controlled rate injection of a therapeutic fluid into the body.

In some embodiments, the present invention's device for medical infusion is thin, has no external tubing and can be adhered to a patient skin (e.g., skin adherable infusion patch).

In some embodiments, the present invention's skin adherable infusion patch includes a reservoir, a delivery tube and an exit port enabling fluid communication with a subcutaneously inserted cannula through a well portion.

In some embodiments, the skin adherable infusion patch includes two parts: a reusable part and a disposable part. The reusable part can include electronic components and the driving mechanism, and the disposable part can include the reservoir, the delivery tube and the exit port.

In some embodiments, a system is provided that includes a skin adherable infusion patch unit having two parts. The infusion patch unit may be attached to the skin directly, using a carrier unit, or using a cradle unit.

In some embodiments, a device is provided that includes a dispensing patch unit that can be disconnected and reconnected.

In some embodiments, a method for medical infusion is provided that allows infusion of a therapeutic fluid into the patient's body through a flexible, soft subcutaneously insertable cannula. The cannula can be inserted into the patient's body manually by the patient or using a spring loaded inserter.

In some embodiments, a reliable, safe, accurate and user-friendly system is provided that includes a skin adherable infusion patch unit.

In some embodiments, a low cost skin adherable infusion patch, according to the present invention, includes two parts: a reusable part and a disposable part, wherein the production cost of the disposable part is low (where the disposable part includes a few relatively inexpensive components).

In some embodiments, the skin adherable infusion patch has a reusable part and a disposable part, where the disposable part contains a transparent reservoir allowing the patient to see amount of fluid during filling and pump operation.

In some embodiments, the skin adherable infusion patch includes a reusable part and a disposable part, where the components of the pump are located in the reusable part. Initial adjustments can be performed in the factory and not by the patient, thereby allowing higher accuracy and performance of the fluid pump.

In some embodiments, the skin adherable infusion patch includes a reusable part and a disposable part, where the connection between the two parts is well-sealed, thereby establishing a water-proof dispensing patch unit that prevents water penetration, leakage or the entrance of contaminants.

BRIEF DESCRIPTION OF DRAWINGS

A detailed description of embodiments of the invention will be made with reference to the accompanying drawings, wherein like reference numerals designate corresponding parts in the several figures, and in which.

DETAILED DESCRIPTION OF THE INVENTION

Figure 1:
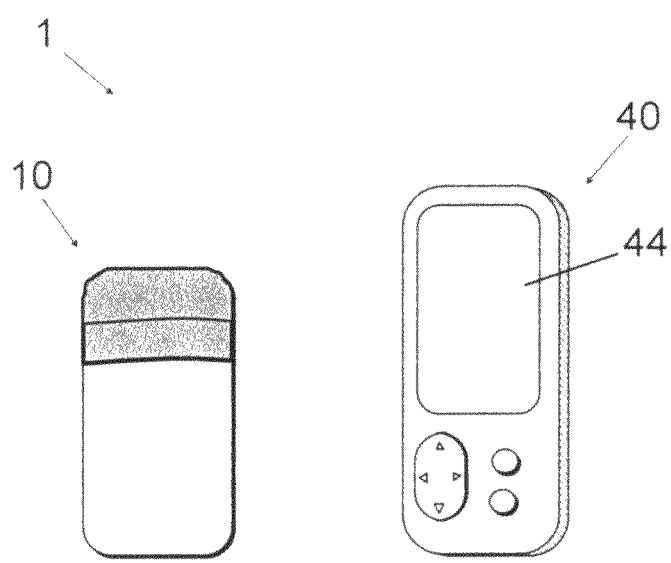
FIG. 1 illustrates an exemplary fluid dispensing device including a dispensing unit and a remote control unit, according to some embodiments of the present invention.

FIGS. 1-6B illustrate a fluid delivery system or device (1) and various possibilities for its attachment to the body. FIG. 1 shows the device (1) for medical infusion of therapeutic fluids into the body. The device (1) includes a dispensing unit (10) and a remote control unit (40). As can be understood by one skilled in the art, the dispensing unit (10) can be in the form of any type of dispensing device, such as a dispensing patch, and that the present invention is not limited to a patch. The terms "dispensing unit" and "dispensing patch" will be used throughout the following description interchangeably and have the same meaning. In some embodiments, the remote control unit (40) can include various controls, a processor, and communications capabilities, that can interact and control operation of the dispensing unit (10). The remote control unit (40) can also include a display screen (44) that can display status and other information for the patient (the terms "patient" and "user" are used in this description). The dispensing unit (10) can also include various controls, a processor, and communication capabilities in addition to other components, which are described below. The dispensing unit's (10) components interact with the remote control unit (40) components for operational purposes.

Figure 2A:
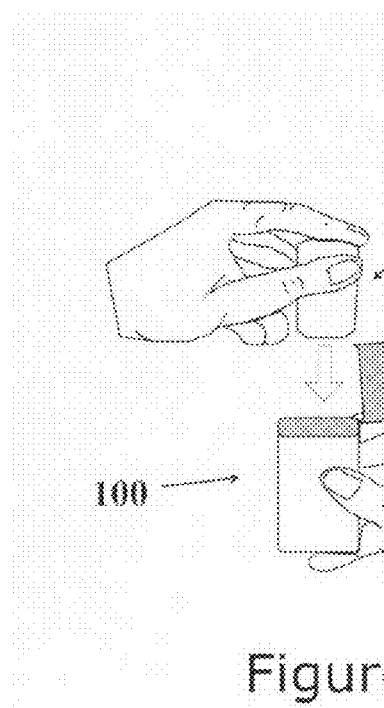
FIGS. 2A-C illustrate an exemplary two-part dispensing unit and disposition of the disposable part within the reusable part, according to some embodiments of the present invention.
Figure 2B:
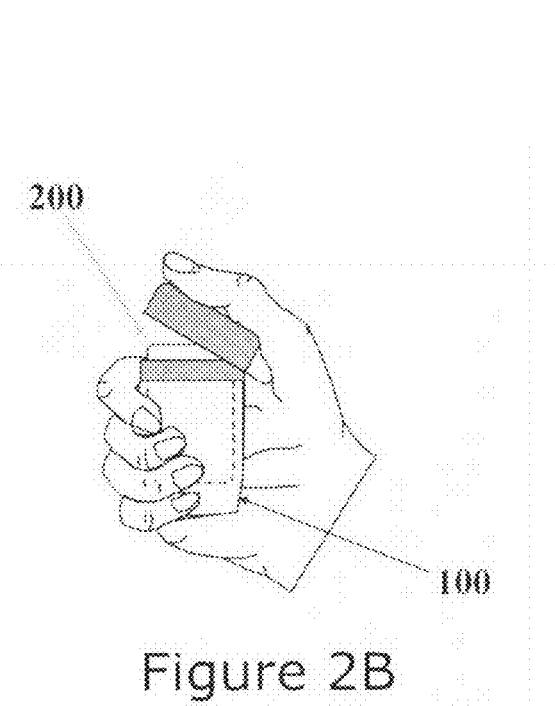
Figure 2C:
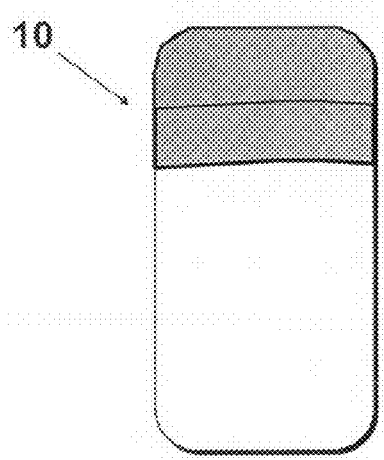

Referring to FIGS. 2A-2C, the dispensing patch unit (10) includes a reusable part (100) and a disposable part (200). The reusable part (100) and the disposable part (200) can be connected to each other, as illustrated in FIG. 2C.

FIGS. 2A-C illustrate connection of the two parts. FIG. 2A shows the insertion of the disposable part (200) into the reusable part (100). FIG. 2B shows the disposable part (200) disposed within the reusable part (100) and cover portion (102) being closed. FIG. 2C shows the dispensing patch unit

(10) when the cover portion (102) is closed and the disposable part (200) is inserted within the reusable part (100).

Figure 3A:
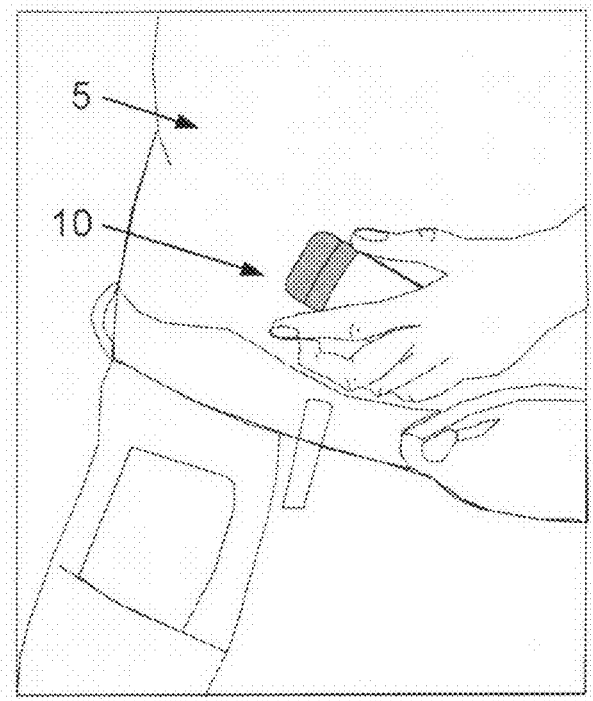
FIGS. 3A-B illustrate an exemplary direct attachment of the dispensing unit onto the body, according to some embodiments of the present invention.
Figure 3B:
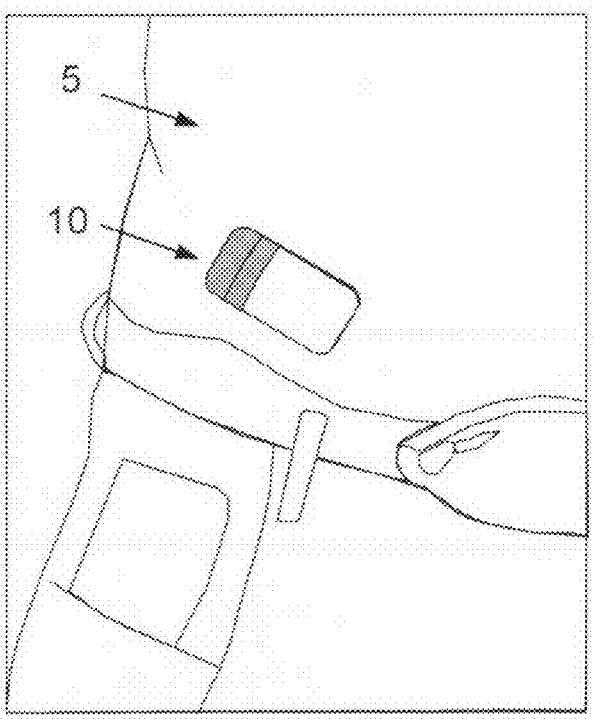

FIGS. 3A-B show an examples of adhering the dispensing patch unit (10) to the skin (5) of a patient. FIG. 3A shows adherence of the dispensing patch unit (10) to the skin (5). FIG. 3B shows the adhered dispensing patch unit (10) being ready for operation.

Figure 4A:
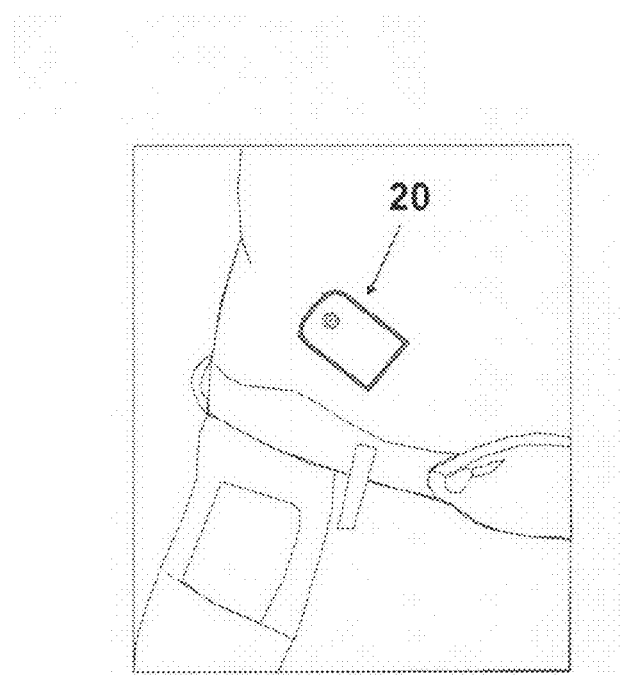
FIGS. 4A-C illustrate an exemplary adherence of the dispensing unit to the patient's skin using a cradle unit, according to some embodiments of the present invention.
Figure 4B:
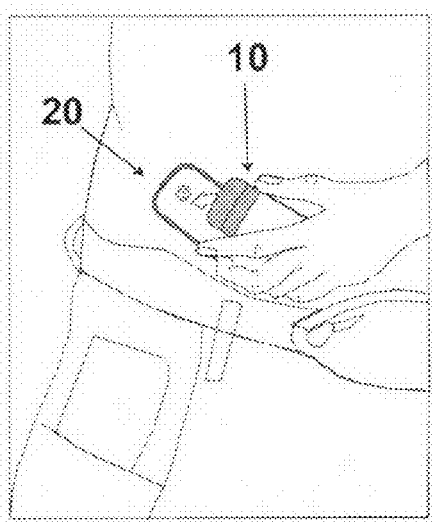
Figure 4C:
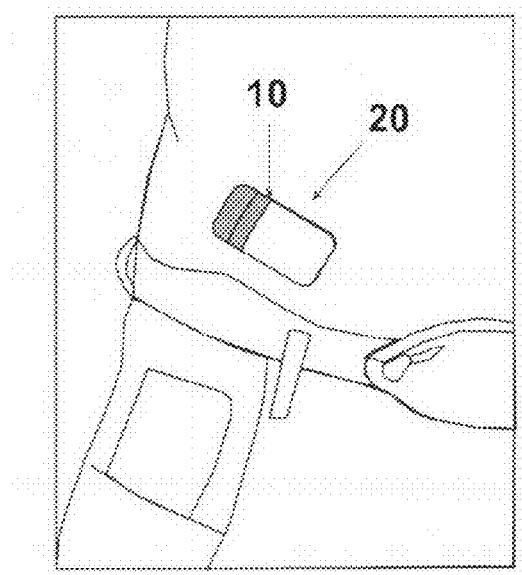

In another embodiment shown in FIGS. 4A-C, a cradle unit (20) can be adhered first to the skin (5) and the dispensing patch unit (10) can be then connected to and disconnected from the cradle unit (20) upon patient's discretion. FIG. 4A shows the cradle unit (20) adhered to the patient's body. FIG. 4B shows the connection of the dispensing patch unit (10) to the cradle unit (20). FIG. 4C shows the dispensing patch unit (10) after it has been connected to the cradle unit (20), being ready for operation.

Figure 5A:
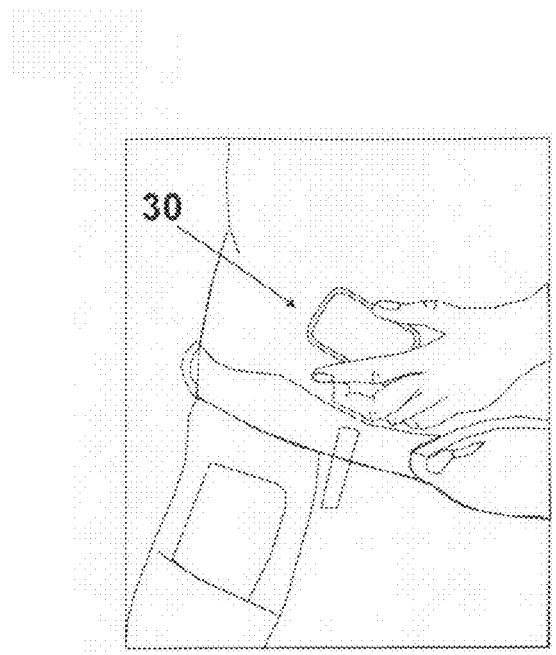
FIGS. 5A-D illustrate an exemplary adherence of the dispensing unit to the patient's skin using a carrier unit, according to some embodiments of the present invention.
Figure 5B:
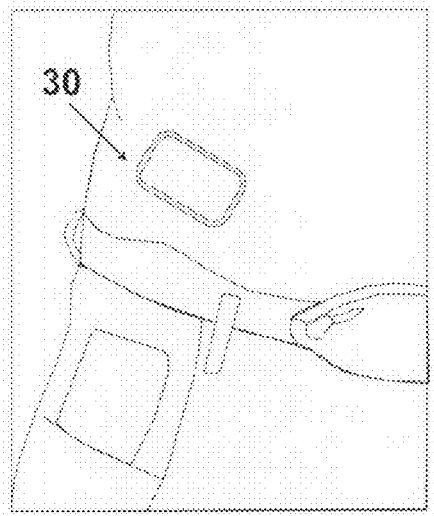
Figure 5C:
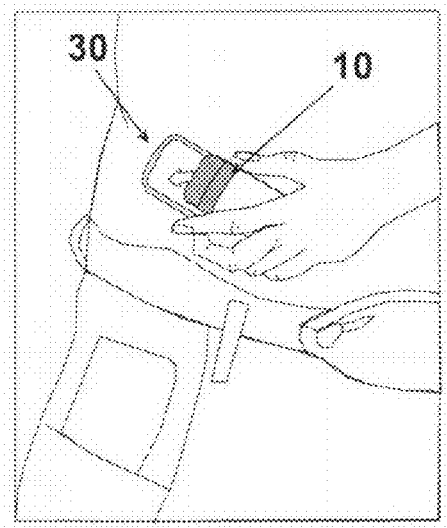
Figure 5D:
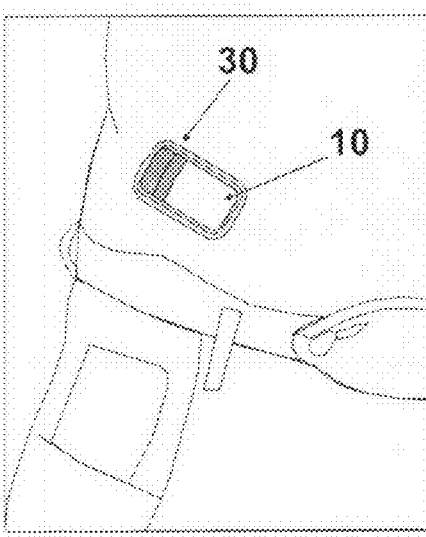

FIGS. 5A-D shows attachment of the dispensing patch unit (10) to the patient using a dedicated carrier unit (30). FIG. 5A shows attachment of the carrier unit (30) to the skin (5). FIG. 5B shows the adhered carrier unit (30). FIG. 5C shows the connection of the dispensing patch unit (10) to the carrier unit (30). FIG. 5D shows the dispensing patch unit (10) connected the carrier unit (30) and ready for operation. As can be understood by one skilled in the art, the cradle unit (30) can be attached the body of the patient at any desired location.

In some embodiments, the carrier unit (30) can be connected to the dispensing unit (10) prior to the cradle unit being adhered to skin (5) of the patient.

Figure 6A:
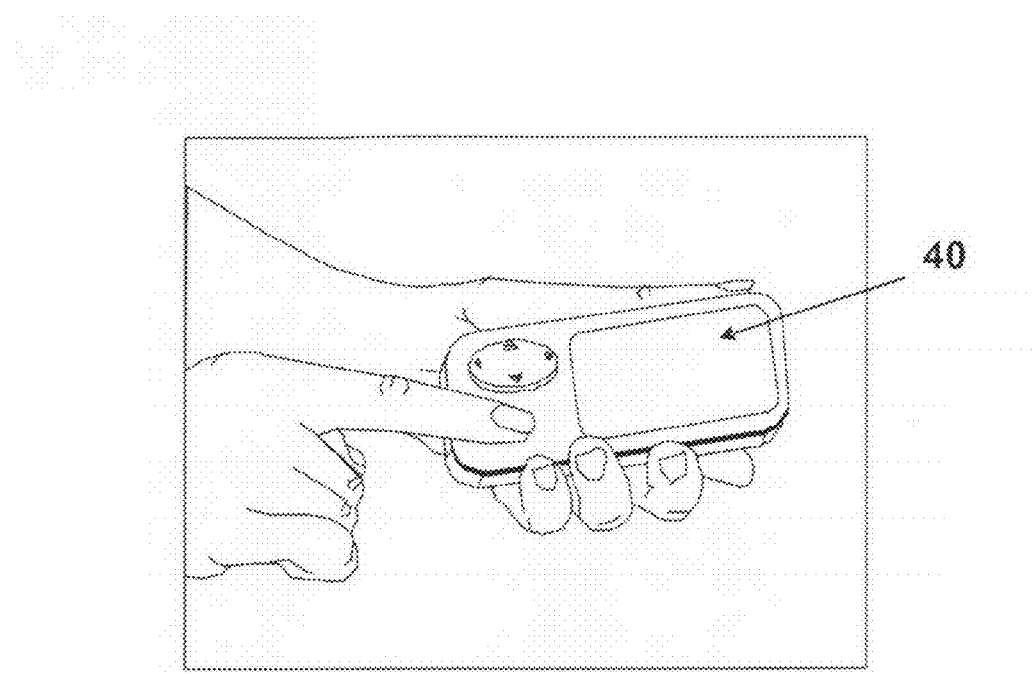
FIGS. 6A-B illustrate exemplary operation modes of the dispensing unit, according to some embodiments of the present invention.
Figure 6B:
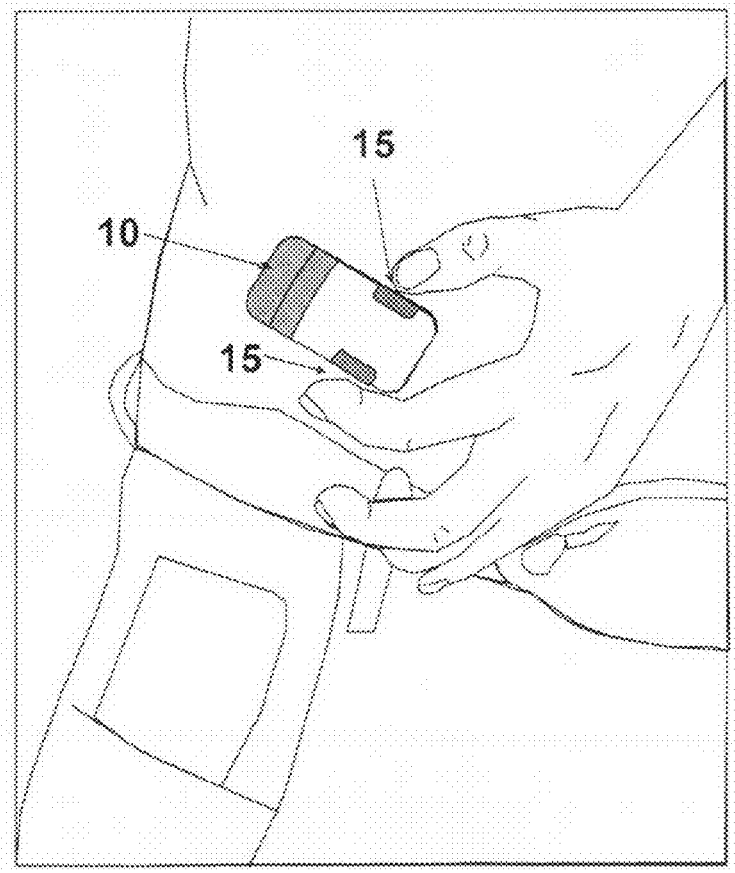

FIGS. 6A-B show modes of operation of the dispensing patch unit (10). The patient can operate the dispensing patch unit (10) either using the remote control unit (40) (shown in FIG. 6A) or using one or more buttons (15) located on the dispensing patch unit (10), as shown in FIG. 6B. The remote control unit (40) can be for example a dedicated remote controller, a cellular phone, a Personal Data Assistant ("PDA"), a watch, a personal computer ("PC"), a laptop, an iPod or any other electronic device suitable for operating the dispensing patch unit.

The remote control unit can communicate with the dispensing patch unit via wireless communication as well as any other suitable methods, for example induction, RF transmission, IR transmission etc., or a wired communication. Communication between the remote control unit and the dispensing patch unit (10) can be unidirectional (i.e., one-way communication) or bi-directional (i.e., two-way communication).

In some embodiments, the remote control unit may include a glucose sensor (not shown in FIGS. 6A-B), which is coupled to the remote control unit. The sensing of glucose concentration levels can be carried out by various sensing techniques, such as, electrochemical, optical or the like. In some embodiments, a blood sample of the patient can be used in association with a conventional test strip that is inserted into a dedicated port, which is located in the remote control unit.

Figure 7A:
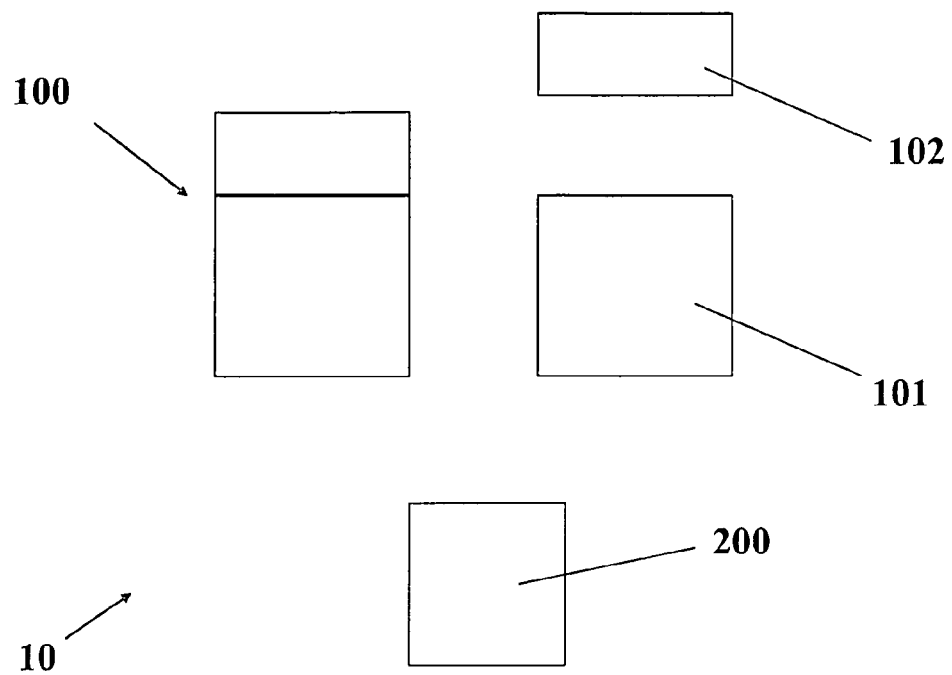
FIGS. 7A-C illustrate an exemplary reusable part containing body and cover, wherein the disposable part can reside within the body portion of the reusable part, according to some embodiments of the present invention.
Figure 7B:
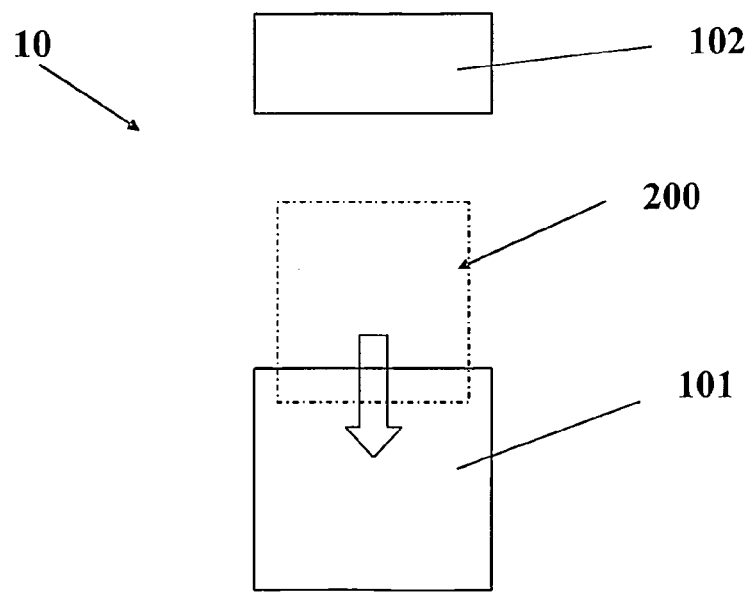
Figure 7C:
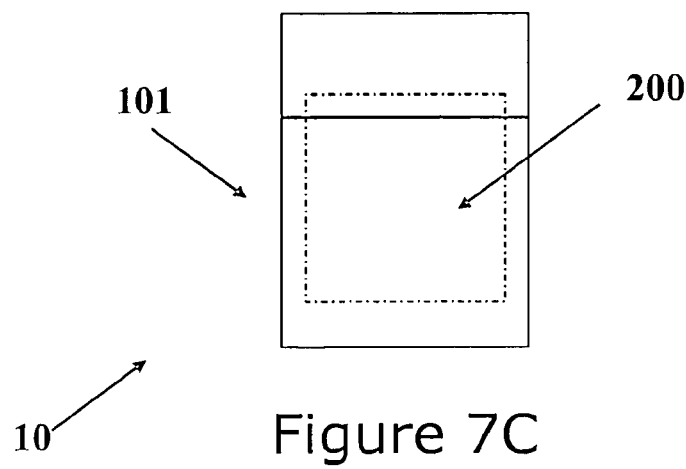

FIGS. 7A-C show the dispensing patch unit (10) having two parts: a reusable part (100) and a disposable part (200).

FIG. 7A shows the reusable part (100) having a body portion (101) and a separate cover portion (102). FIG. 7A also shows the disposable part (200) that can be configured to be smaller in size than the reusable part (100) so that it can be disposed inside the reusable part (100). FIG. 7B shows the insertion of the disposable part (200) into the reusable part (100). To insert the disposable part (200) into the reusable part (100), the cover portion (102) is removed from the reusable part (100), i.e., it is detached from the body portion (101). In some embodiments, the disposable part (200) is a cassette that can enter the cavity of the body portion (101) of the reusable part (100). FIG. 7C shows the disposable part (200) disposed within the body portion (101) of the reusable part (100) and the cover portion (102) is re-attached to the body portion (101) and is closed. Dispensing patch unit (10) operation is possible only when the cassette-like disposable part (200) is properly positioned within the body portion (101). To achieve proper matching, the cassette-like disposable part (200) and the body portion cavity (101) are configured to permit smooth sliding of the disposable part (200) into the body portion (101).

Figure 8A:
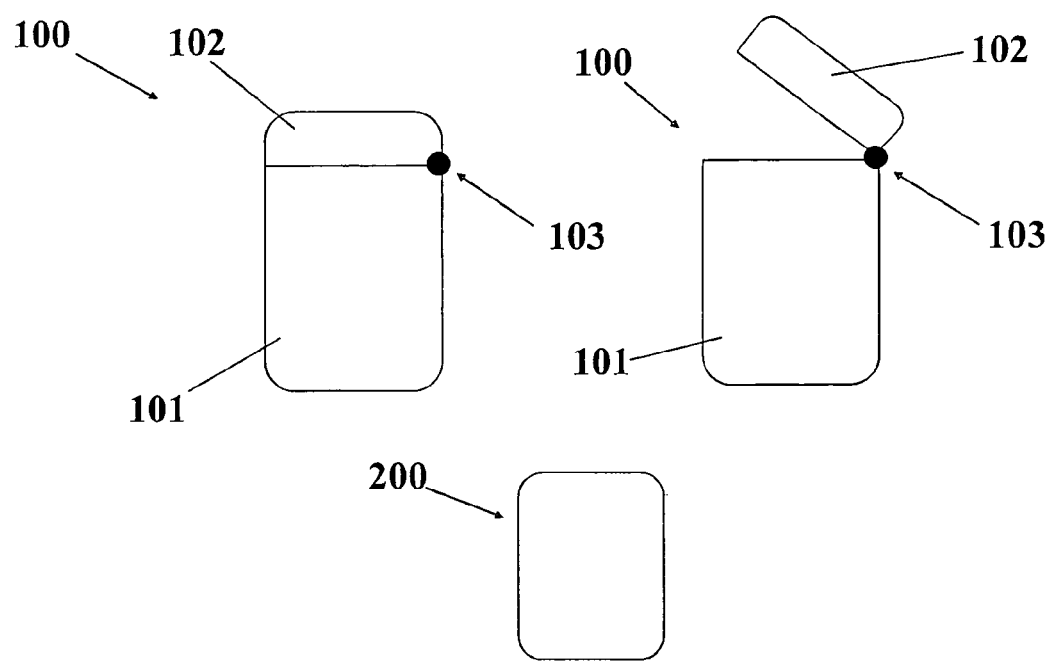
FIGS. 8A-C illustrate exemplary reusable part, including a cover, and the disposable part, wherein the cover and body of reusable part are joined by a hinge, according to some embodiments of the present invention.
Figure 8B:
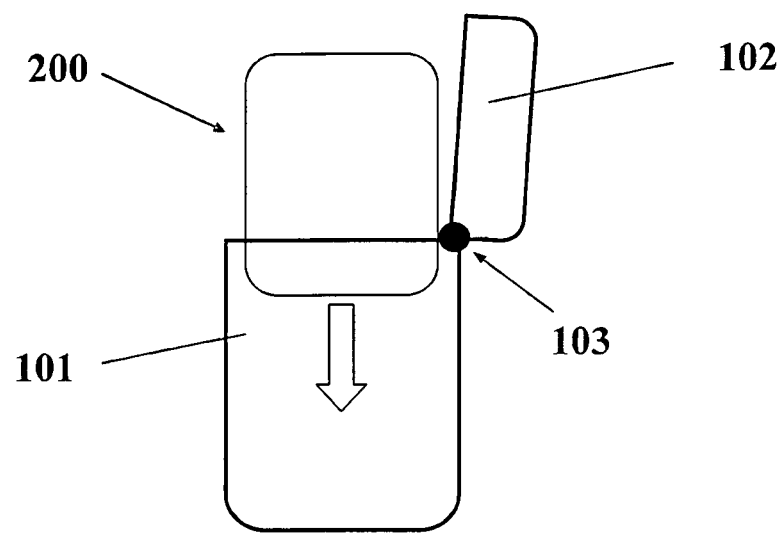
Figure 8C:
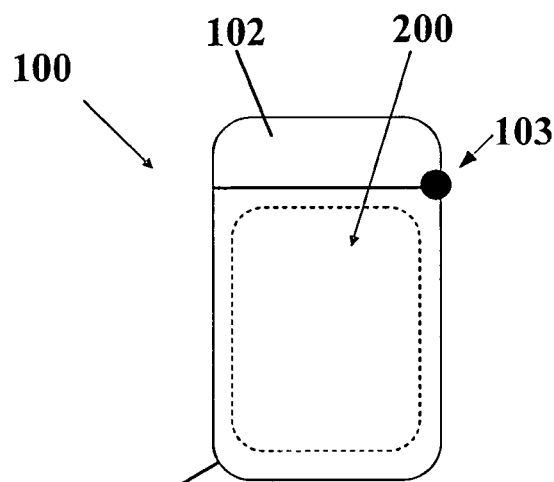

FIGS. 8A-C show an embodiment of the present invention, wherein the body portion (101) and the cover portion (102) of the reusable portion (100) are joined by a hinge or a pivot (103) to enable pivoting of the cover portion (101). FIG. 8a shows the closed reusable part (100) (on the left side of FIG. 8A) and opened reusable part (100) (on the right side of FIG. 8A) and the disposable part (200) (on the bottom of FIG. 8A). As illustrated in FIG. 8A, the pivot (103) is disposed on the right side of the reusable part (100). As can be understood by one skilled in the art, the pivot (103) can be disposed on either side of the reusable part (100) and can be designed to be disposed along the entire length of one side of the reusable part (100). FIG. 8B shows insertion of the disposable part (200) into the body portion (101) of the reusable part (100). The cover portion (102) is swung open, thereby exposing interior of the body portion (101) and the disposable part (200) is inserted into the body portion (101). Subsequent to insertion, the cover (102) is closed. FIG. 8C shows the disposable part (200) being disposed within the reusable part (100), and the cover (102) being closed.

Figure 9A:
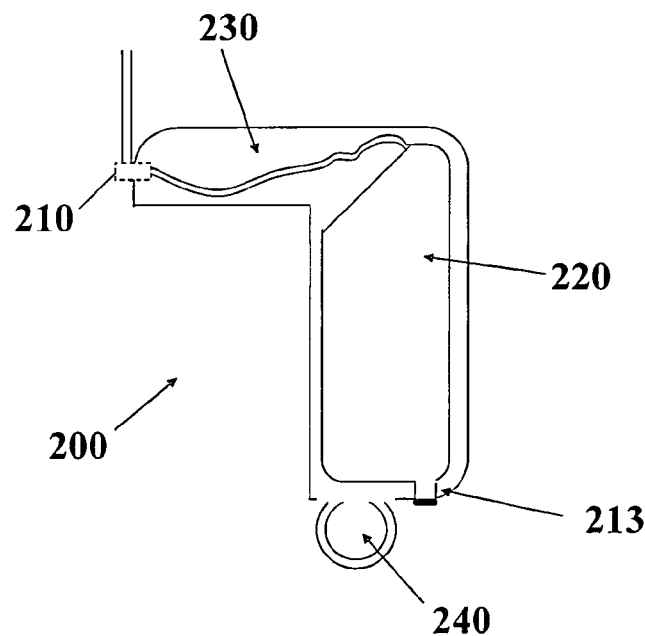
FIGS. 9A-D illustrate an exemplary disposable part, during filling and priming procedures, according to some embodiments of the present invention.

FIGS. 9A-D show additional detail of an exemplary embodiment of the disposable part (200) and a reservoir (220) during filling and priming procedures. FIG. 9A shows components of the disposable part (200), which include a reservoir (220), a filling port (213), a delivery tube (230), and a battery (240). The filling port (213) is in fluid communication with the reservoir (220) and allows filling of the reservoir (220) with therapeutic fluid, e.g., insulin. The reservoir (220) is in fluid communication with the delivery tube (230), through which therapeutic fluid is delivered to an exit port (210) for further deliver to the patient via, for example, a cannula (not shown in FIGS. 9A-D). In some embodiments, the filling port (213) includes a blocking device, such as a rubber septum, that prevents escape of fluid from the reservoir (220) via the filling port (213). The battery (240) is coupled outside of the reservoir (220) and powers up the device (10).

Figure 10A:
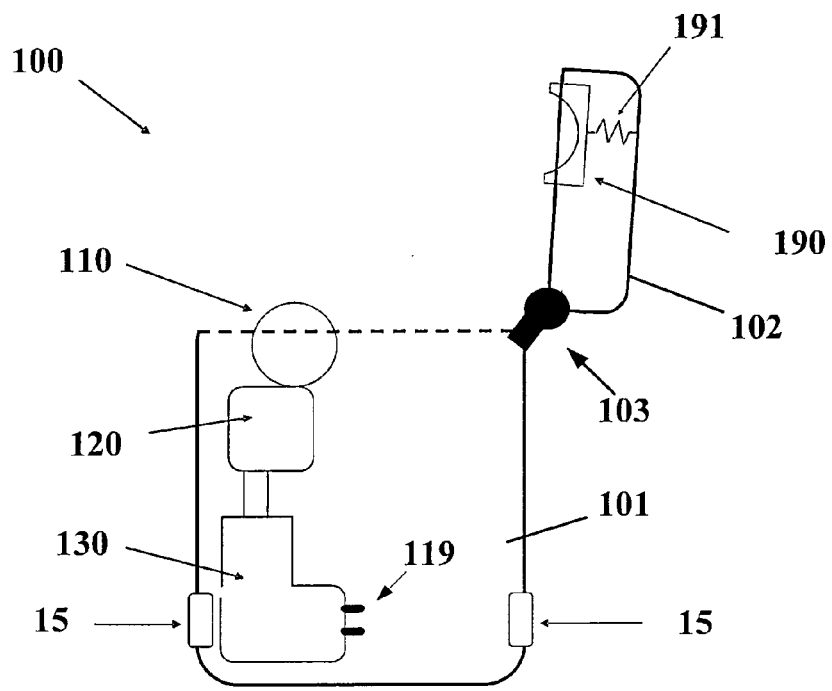
FIGS. 10A-C illustrate exemplary reusable and disposable parts and their connection, according to some embodiments of the present invention.
Figure 10B:
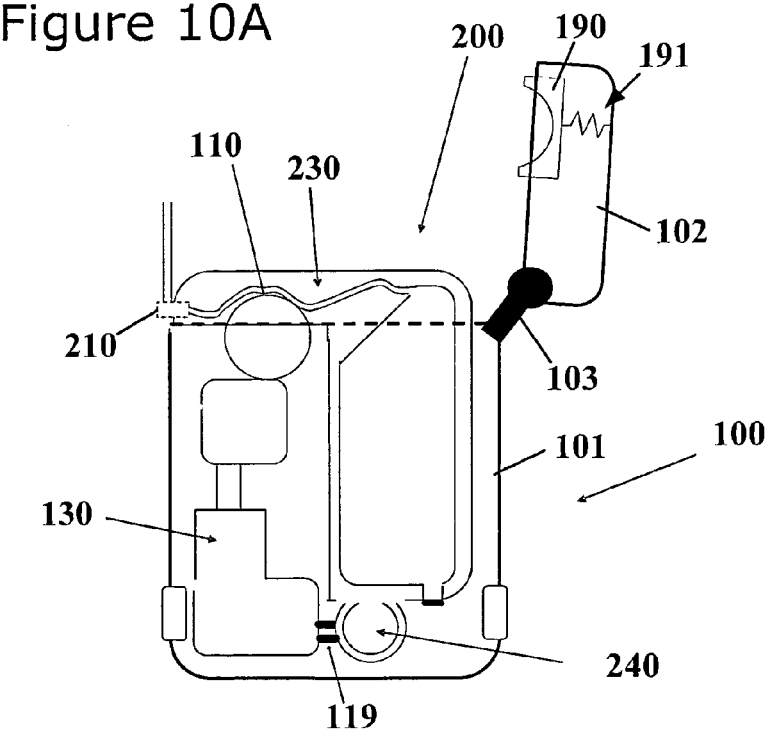
Figure 10C:
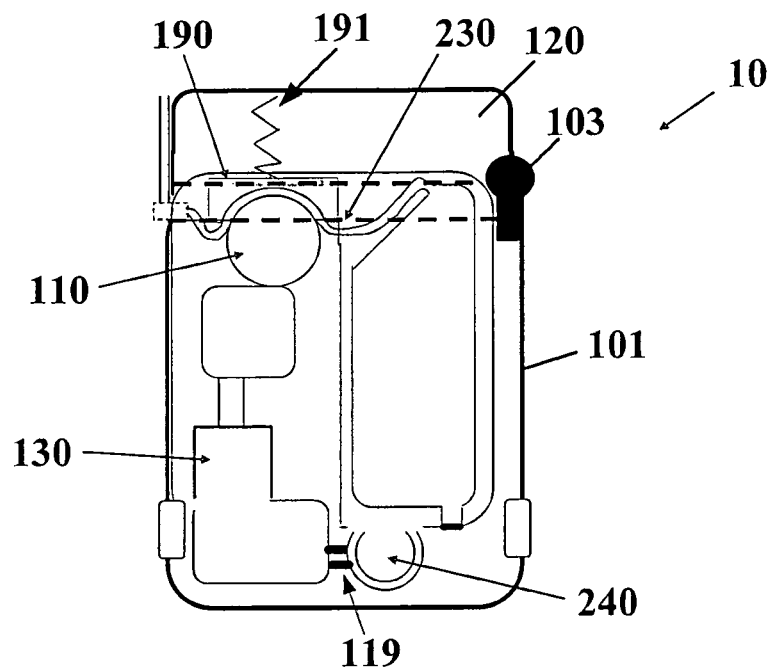

In the above embodiments, a stator (not shown in FIG. 9A) can be disposed in the reusable part (as illustrated in FIGS. 10A-C below) as opposed to being disposed in the disposable part of the device (10). In some embodiments, the disposable part (200) located within the body portion (101) of the reusable part (100) can be without a housing as the housing of the reusable part protects disposable part and its components.

Figure 9B:
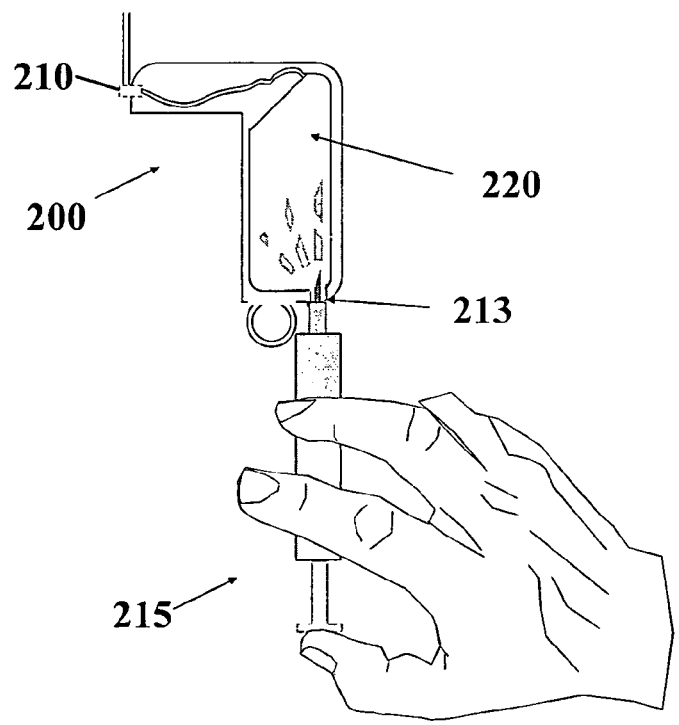
Figure 9C:
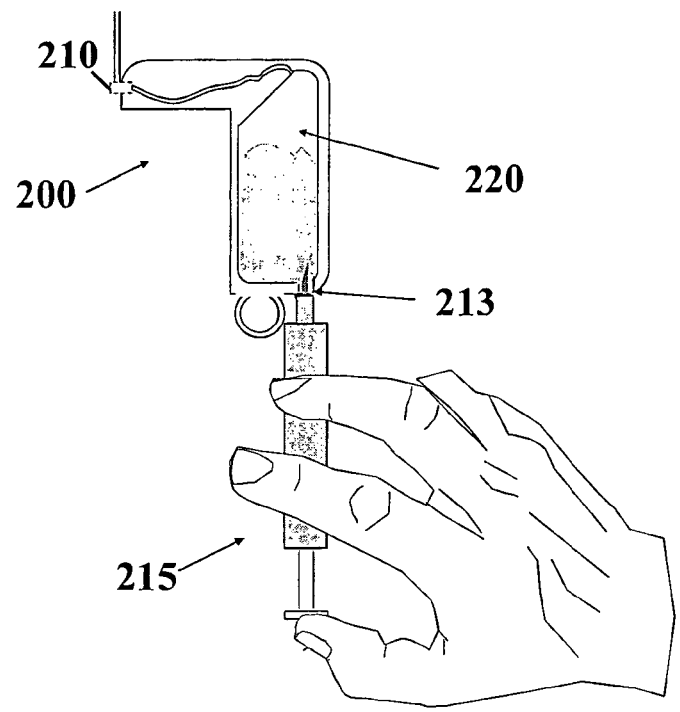
Figure 9D:
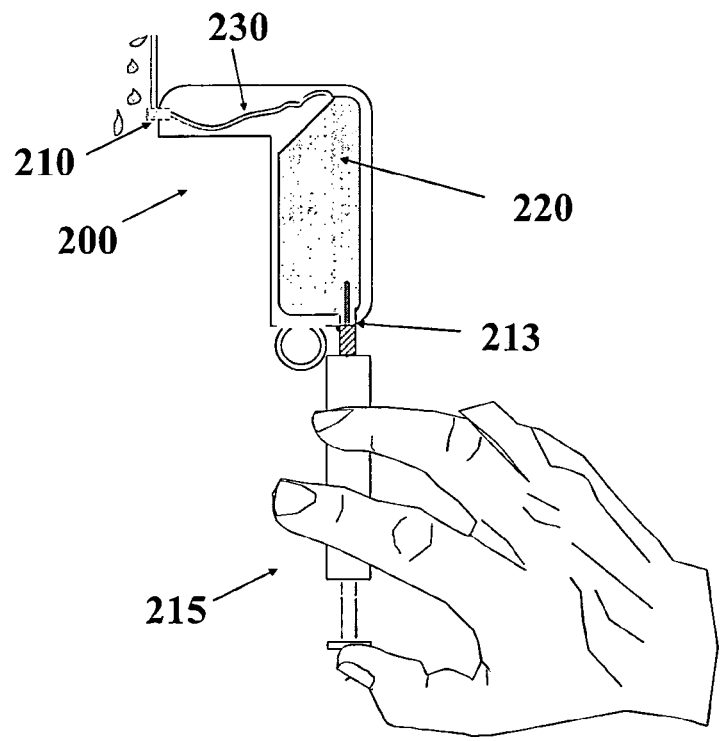

In some embodiments, a need for a single reusable housing can be a major cost reduction factor, thereby significantly lowering the cost of manufacturing the device (10) as well as ultimate cost to the consumer. In addition, at least a portion of the reusable part's (100) housing can be transparent to allow the patient to continuously monitor level and/or content of the fluid inside the reservoir (220). FIGS. 9B-D show filling and priming procedures. FIGS. 9B-C show reservoir (220) being filled with a syringe (215) through the filling port (213). In some embodiments, an adapter (not shown in FIGS. 9A-D) can be used to connect the syringe (215) and the filling port (213). An example of such connection is detailed in a commonly-owned patent application U.S. Provisional Patent Application Ser. No. 60/838,660, filed Aug. 18, 2006, and International Patent Application No. PCT/IL07/001027, filed Aug. 16, 2007. Subsequent to the attachment of the syringe (215) to the filling port (213), the contents of the syringe (215) are transferred to the reservoir (220) (typically, under pressure from pressing on a plunger of the syringe). As stated above, the user may be able to observe the reservoir (220) being filled, as illustrated in FIG. 9C.

FIG. 9D shows a priming procedure, which is performed subsequently to filling the reservoir (220). During the priming procedure, the disposable part (200) is held in an upright position and the fluid pressure created by the user pressing on the plunger of the syringe, forces air bubbles/pockets out of the reservoir (220) and the delivery tube (230) filling. The priming procedure is performed until the fluid begins to drip from the exit port (210), as shown in FIG. 9D.

FIGS. 10A-C show in detail a connection of the reusable and disposable parts. FIG. 10A shows the reusable part (100) and its components. The components include a linear positive displacement pump structure that is composed of a rotary wheel (110) with rollers (not shown in FIG. 10A), a motor (120) with gear(s) (not shown in FIG. 10A), a stator (190) and a printed circuit board ("PCB") (130). The PCB (130) is coupled to the motor (120), which forces rotation of the rotary wheel (110). Upon rotation of the rotary wheel, the rollers disposed inside the rotary wheel interact with the stator (190). In some embodiments, the stator (190) can be disposed within the cover (102), whereas the remaining components of the linear positive displacement pump can be disposed inside the body portion (101) of the reusable part (100). The stator (190) is further coupled to a spring (191), which is, in turn, coupled to the cover (102). The spring (190) creates tension and allows the stator (190) to press against the delivery tube (230), as shown in FIG. 10C, when the disposable part (200) is inserted into the reusable part (100) and the cover (102) is closed.

The reusable part (100) further includes two buttons (15) that allow manual operation of the dispensing patch unit (10) (e.g., without the remote control unit (40)). The function of the buttons (15) can vary and can include turning on/off the device (10), programming/causing the device (10) to inject a bolus dose and/or basal dosage of therapeutic fluid (e.g., insulin) to the patient, or any other function. Each button (15) can be assigned its own function. In some embodiments, the two buttons can be assigned with the same function (e.g. injection of a bolus dose) for safety reasons, preventing unintentionally pressing.

FIG. 10B shows the disposable part (200) being inserted into the reusable part (100). The cover (102) is swung open using hinge/pivot (103) and the interior portion of the body (101) is exposed. The disposable part (200) is then inserted inside the body portion (101). Upon insertion, the battery (240) connects to the PCB (130) using electrical contacts (119) and the delivery tube (230) overlays the rotary wheel (110), as illustrated in FIG. 10B. Upon connection of the battery (240) to the PCB (130), the device (10) can be powered up.

FIG. 10C shows the dispensing patch unit (10) subsequent to placement of the disposable part (200) within the body portion (101) of the reusable part (100) and after closing the cover portion (102). As stated above, in this position, the battery (240) is electrically connected to the board (130) and power is supplied for energizing electronic components and the rotary wheel (110). Furthermore, the rotary wheel (110) is juxtaposed (i.e., being placed close together or side-by-side) with the stator (190) (supported by the spring (191)) in way that it squeezes the delivery tube (230) against the wheel (110) allowing peristaltic pumping of the fluid.

The location of the stator (190) within the cover portion (102) of the reusable part provides accuracy and reliable interaction between the rotary wheel (110), the delivery tube (230) and the stator (190). It further eliminates inaccuracies due to assembly and manufacturing tolerances.

The exit port (210) can be configured to protrude outside the reusable part (100), as illustrated in FIG. 10C. This way, upon operation of the device (10), therapeutic fluid is being pumped from the reservoir (220) into the delivery tube (230), wherein a portion of the delivery tube (230) is being placed between the stator (190) and the rotary wheel (110), and further delivered to the exit port (110) for further delivery to the patient via a cannula. Various rotation speeds/frequencies of the rotary wheel (110) and/or rollers disposed within the rotary wheel (110) along with the pressure applied by the stator (190) can determine the amount of therapeutic fluid delivered to the patient (e.g., basal vs. bolus doses).

Figure 11A:
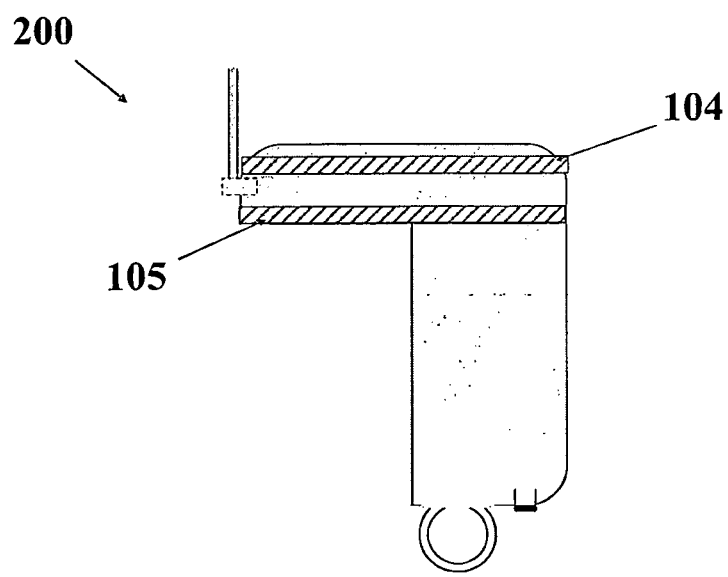
FIGS. 11A-D illustrate an exemplary sealing mechanism of the dispensing unit, according to some embodiments of the present invention.

FIGS. 11A-D show an exemplary embodiment of the dispensing patch unit (10) sealing mechanism. FIG. 11A shows the disposable part (200) including two gaskets (e.g., rubber O-rings): an upper gasket (104) and a lower gasket (105). In some embodiments, the gaskets (104) and (105) can be disposed around portions of the reservoir (220) as well as portions of the delivery tube (230). Further the gaskets (104) and (105) can be configured to match the perimeter of the body portion (101) and the cover (102).

Figure 11B:
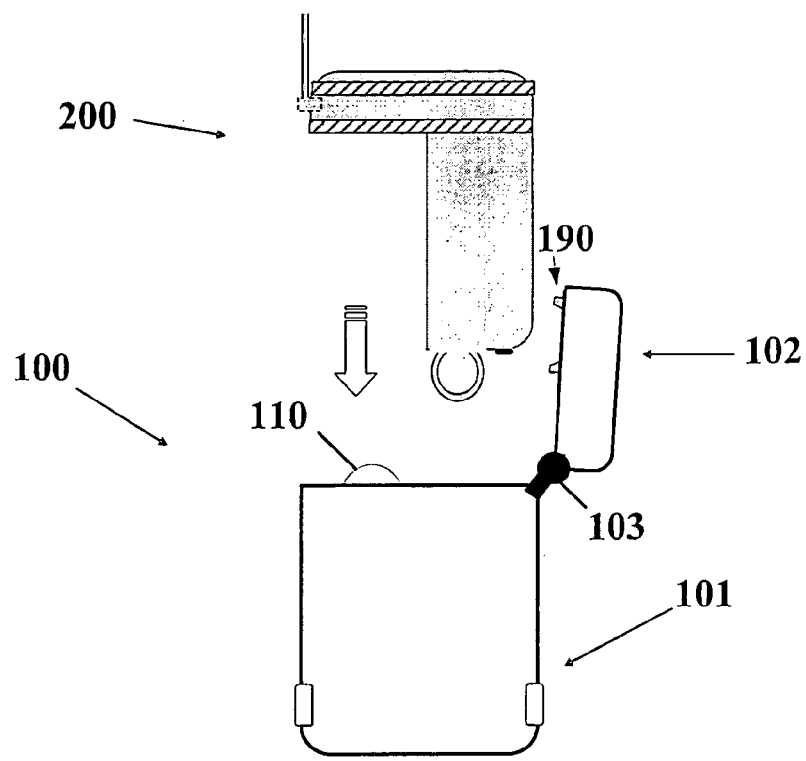
Figure 11C:
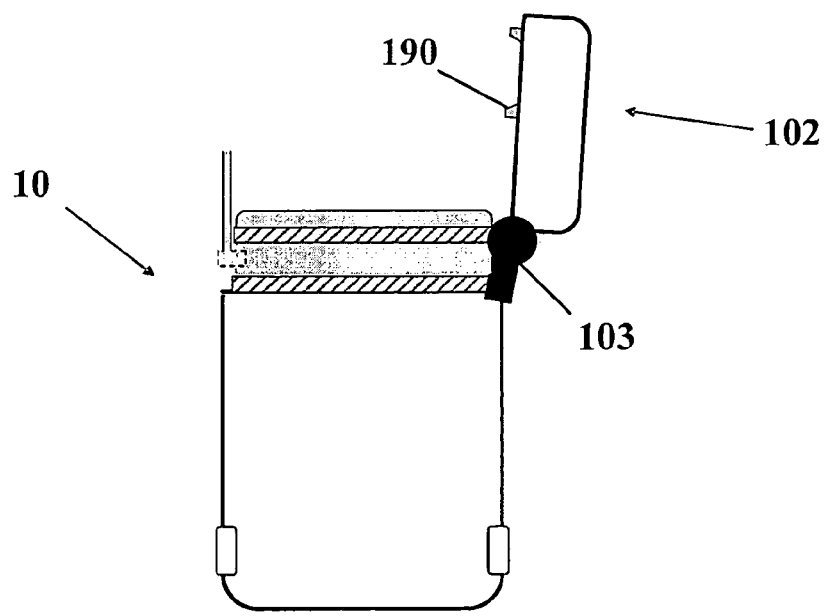
Figure 11D:
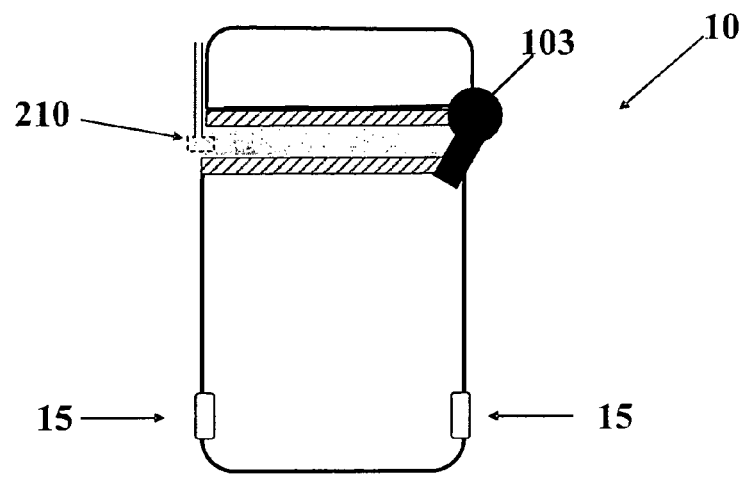

FIG. 11B shows disposable part (200) and the reusable part (100) being connected. The gaskets (104) and (105) maintain sealing of the dispensing patch unit (10) after positioning the disposable part (200) within the reusable part (100) and after pivoting the cover portion (102) to close the body portion (101). FIG. 11C shows the dispensing patch unit (10) when the body portion (101) is opened. FIG. 11D shows the dispensing patch unit (10) with the body portion (101) closed by the cover portion (102). Because the gaskets (104) and (105) match the perimeters of the body portion (101) and the cover (102), the dispensing patch unit (10) is completely sealed and fluid delivery is allowed from the reservoir (220) through the exit port (210). In some embodiments, the buttons (15) can become operable upon closing of the cover (102), which insures that a sealed connection between the cover (102) and the body portion (101) is created.

Figure 12A:
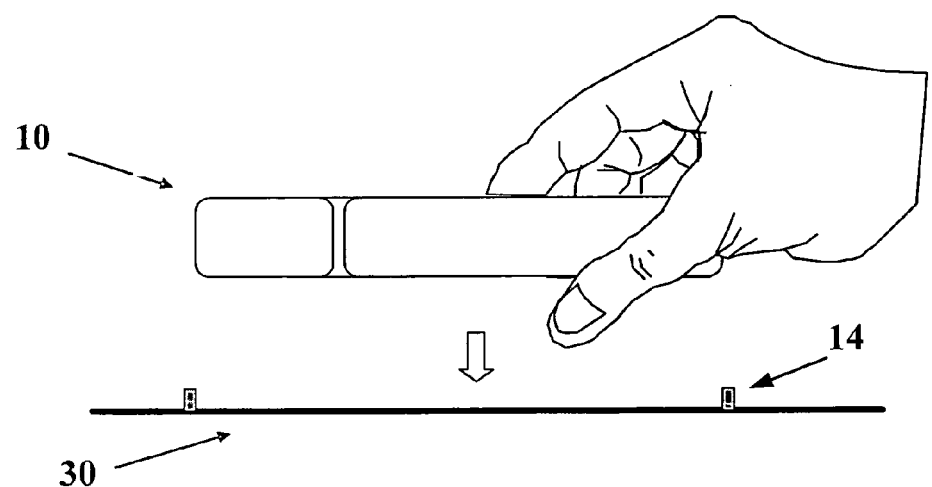
FIGS. 12A-H illustrate an exemplary adherence of the dispensing unit to the body of the patient using a carrier unit, according to some embodiments of the present invention.
Figure 12B:
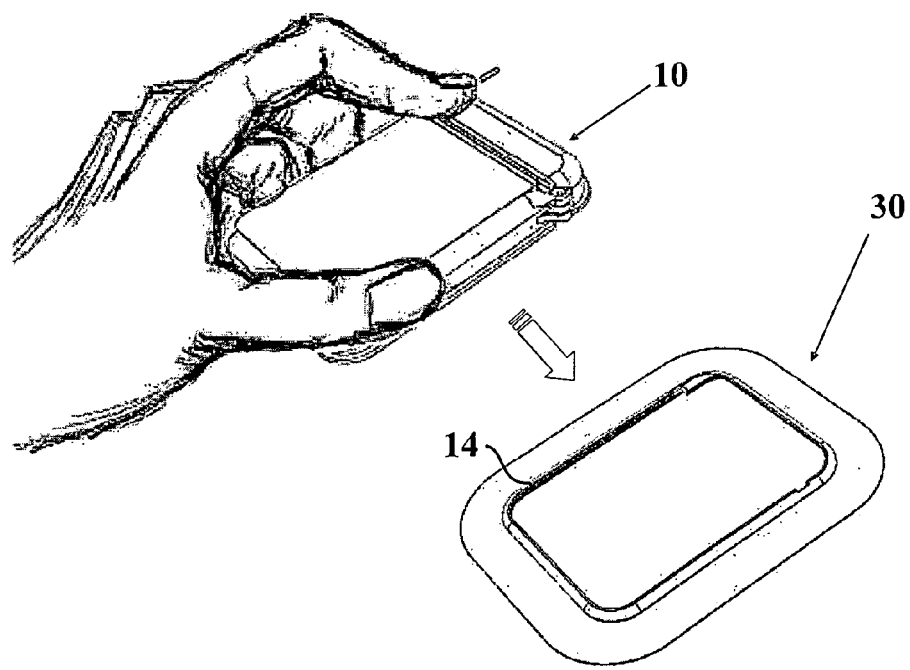
Figure 12C:
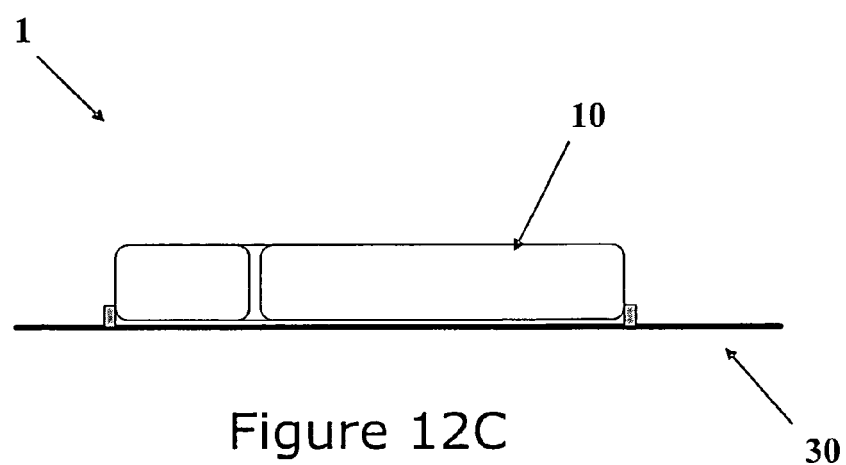
Figure 12D:
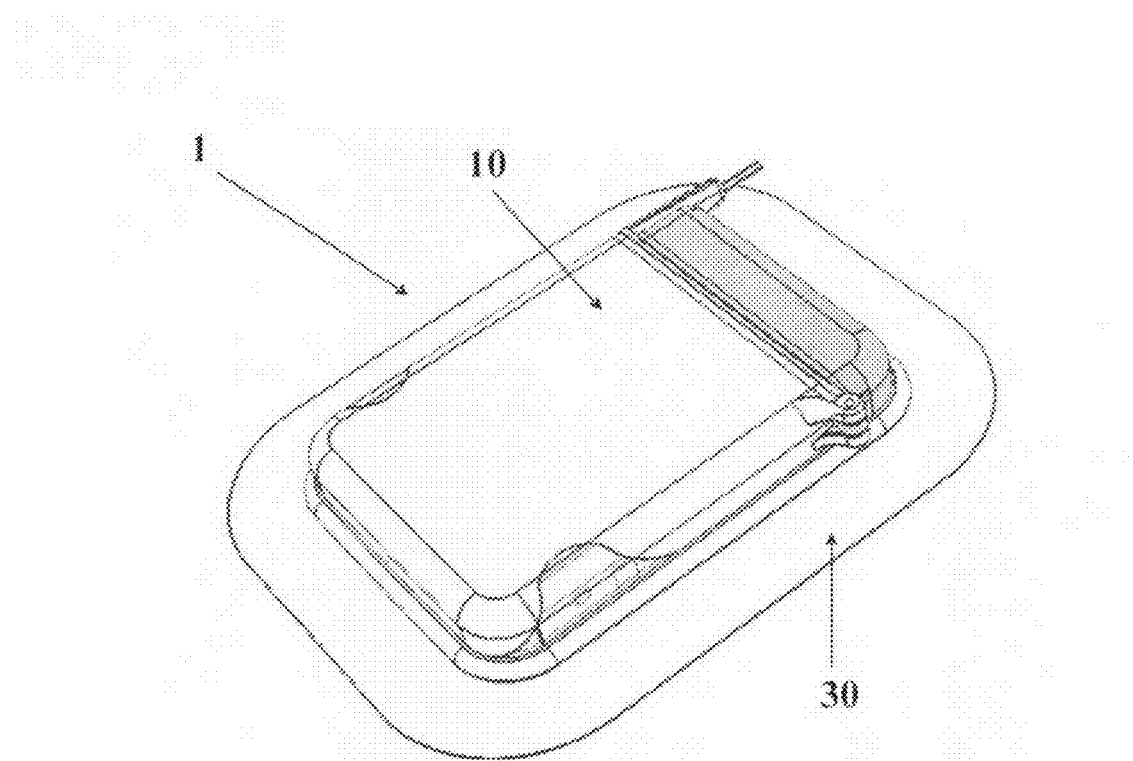
Figure 12E:
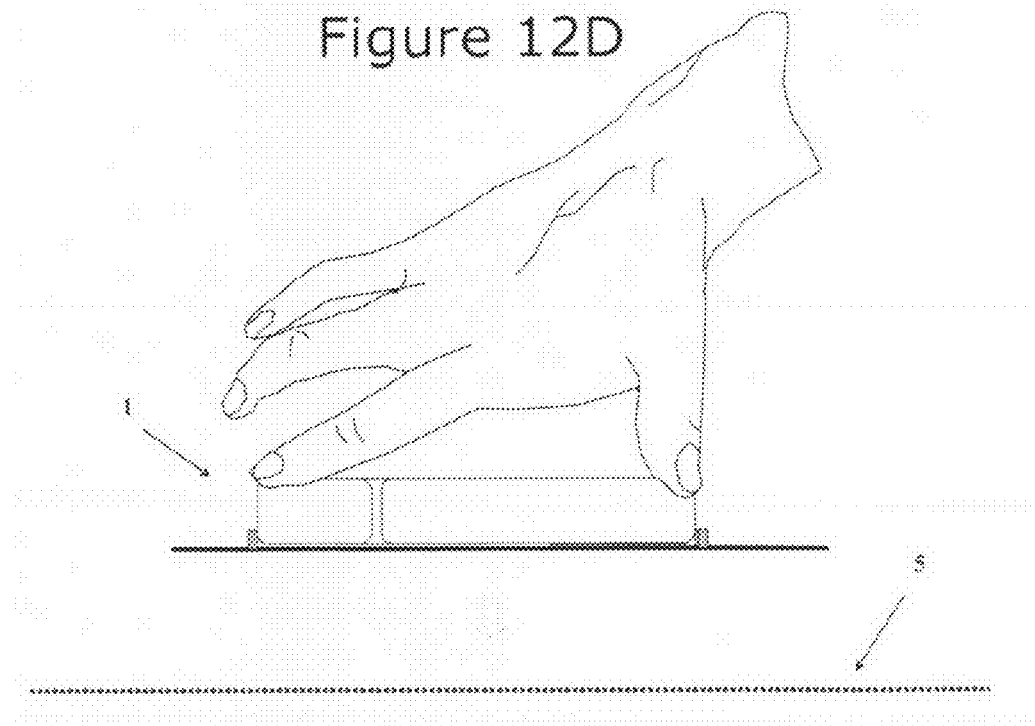
Figure 12F:
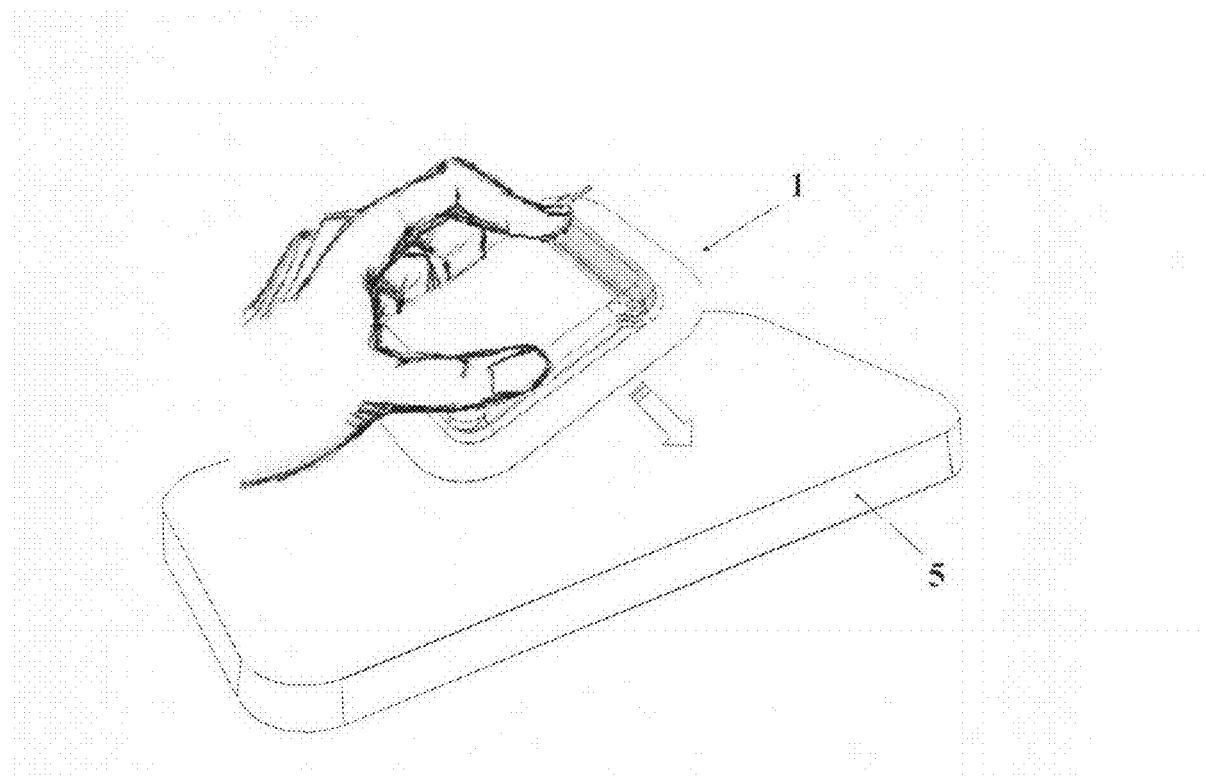
Figure 12G:
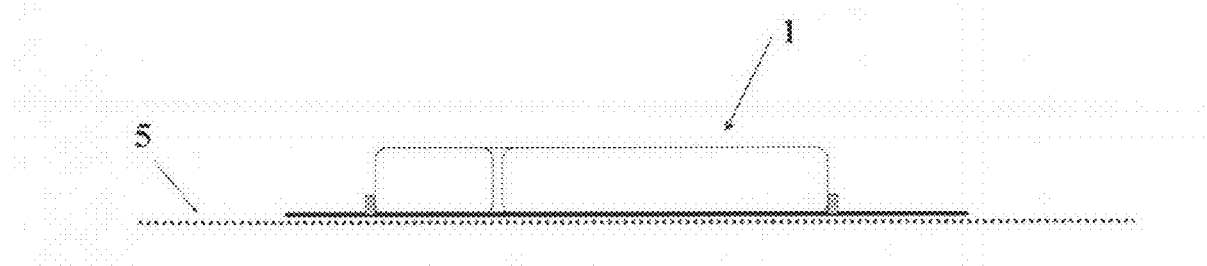
Figure 12H:
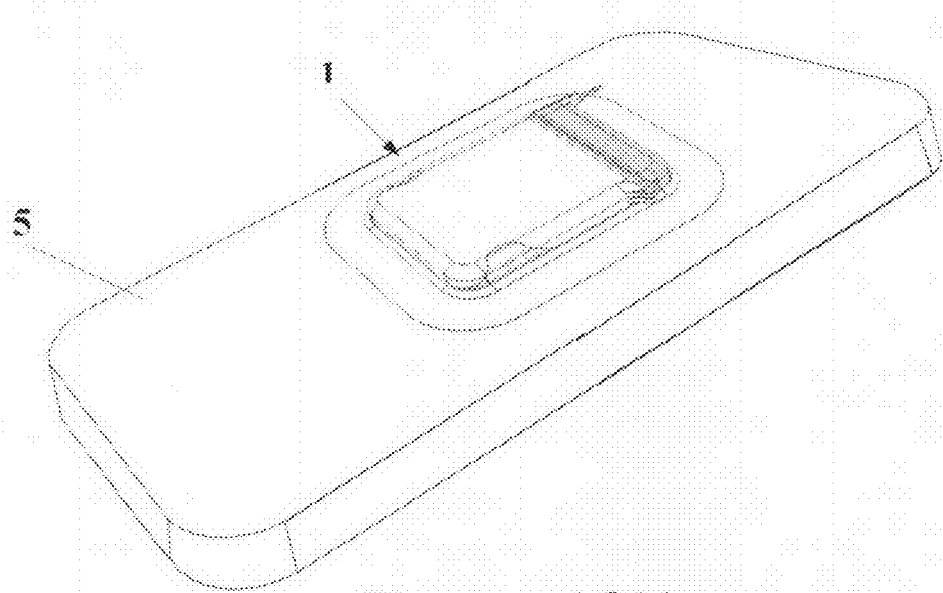

FIGS. 12A-H shows an embodiment of the dispensing patch unit (10) attached to the body of the patient using a carrier unit (30). The carrier unit (30) is a frame with an adhesive that connects to the skin (5). The adhesive can be disposed on the bottom portion of the frame. The carrier unit (30) serves as a carrier for the dispensing patch unit (10) and allows connection and disconnection therebetween. FIGS. 12A-B show connection of the dispensing patch unit (10) to the carrier unit (30). The frame of the carrier unit (30) further includes a border (14) that surrounds an area configured to accommodate placement of the dispensing unit (10), as illustrated in FIGS. 12C-D. FIGS. 12C-D show the dispensing patch unit (10) connected to the carrier unit (30). In this configuration the dispensing patch unit (10) and the carrier unit (30) constitute the fluid delivery device (1). The dispensing unit (10) can be secured to the carrier unit (30) by way of snap-on or any other suitable mechanisms. FIGS. 12E-F show how the device (1) is being adhered to the skin (5). The adhesive layer (not shown in FIGS. 12E-F), is secured to the skin (5) of the patient, thereby securing the carrier unit (30) to the skin of the patient. The adhesive layer can allow multiple attachments (i.e., multi-use adhesive) or a single-use attachment (i.e., a single use adhesive). FIGS. 12G-H are a side view and a perspective view, respectively of the device (1) being affixed to the skin (5).

Figure 13A:
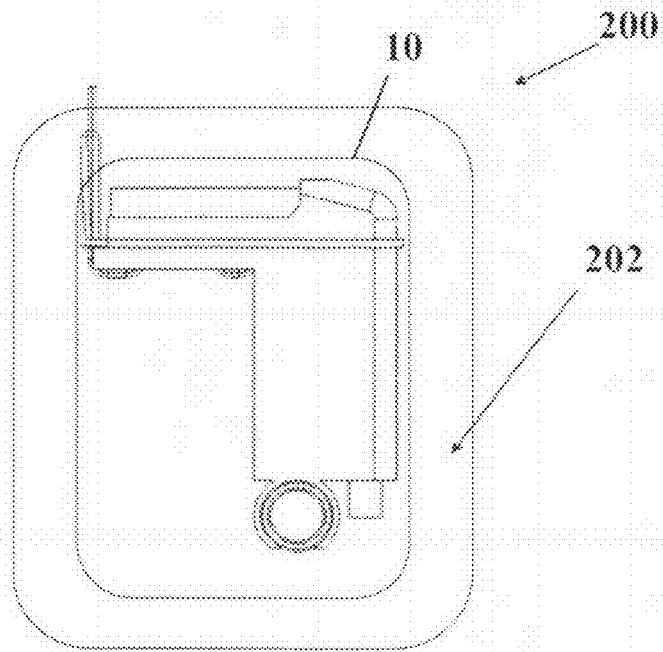
FIGS. 13A-B illustrate an exemplary carrier portion that is attached to the disposable part and serves as the carrier for the dispensing patch unit, according to some embodiments of the present invention.
Figure 13B:
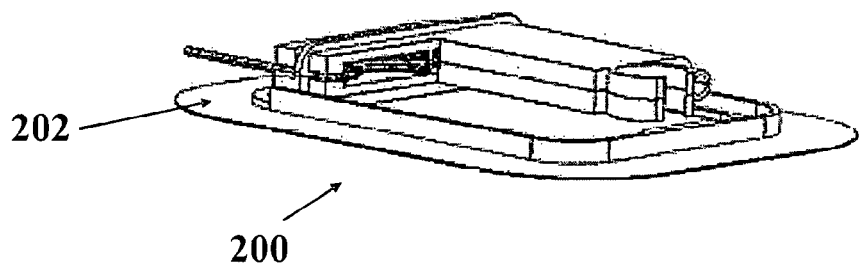

FIGS. 13A-B show another exemplary dispensing patch unit (10), according to some embodiments of the present invention. In these embodiments, the disposable unit (200) can be directly coupled to the carrier portion, which is, in turn, secured to the skin of the patient. Referring to FIGS. 13A-B, a carrier portion (202) is attached to the disposable part (200). One should bear in mind, however that after connection of the reusable (100) and disposable (200) parts, the dispensing patch unit (10) can be adhered directly to the skin (5). The disposable part (200) (for example, with a unitary carrier) can be received, at least in part, within the reusable part (100). In some embodiments, the unit (10) cannot operate without reusable part being attached to the disposable part (200). One of the problems with conventional adhesives is that most of them are designed for a single-use only, as such, adherence of the reusable part's (100) components to the user's skin may be undesirable. One of the advantages of the embodiment shown in FIGS. 13A-B, is that it reduces a number of components in the system, provides the user with a simple and efficient way to attach the device, as well as reduces the cost of manufacturing the device and the ultimate cost to the user.

Figure 14A:
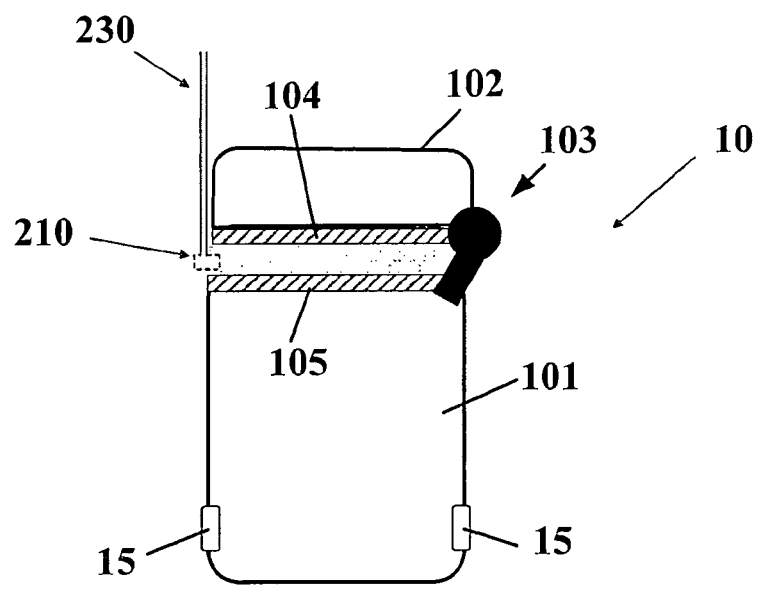
FIGS. 14A-D illustrate an exemplary dispensing device, wherein the delivery tube extends from the dispensing patch unit connected to an infusion set, according to some embodiments of the present invention.
Figure 14B:
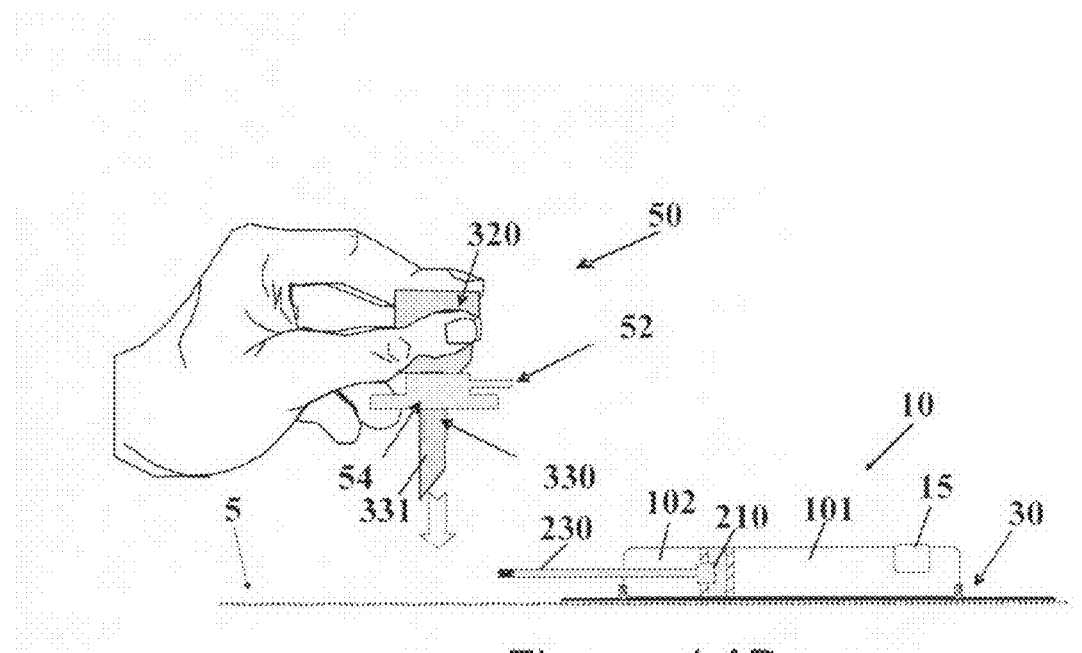
Figure 14C:
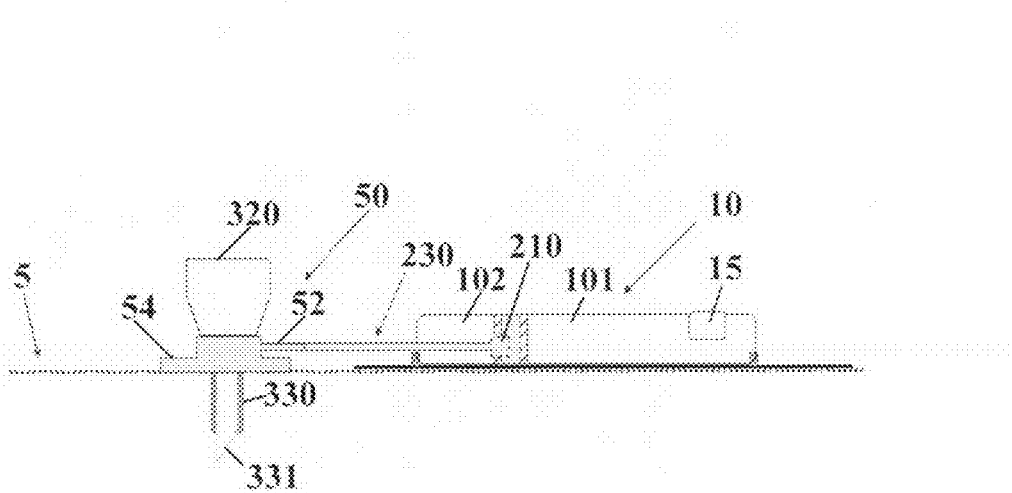
Figure 14D:
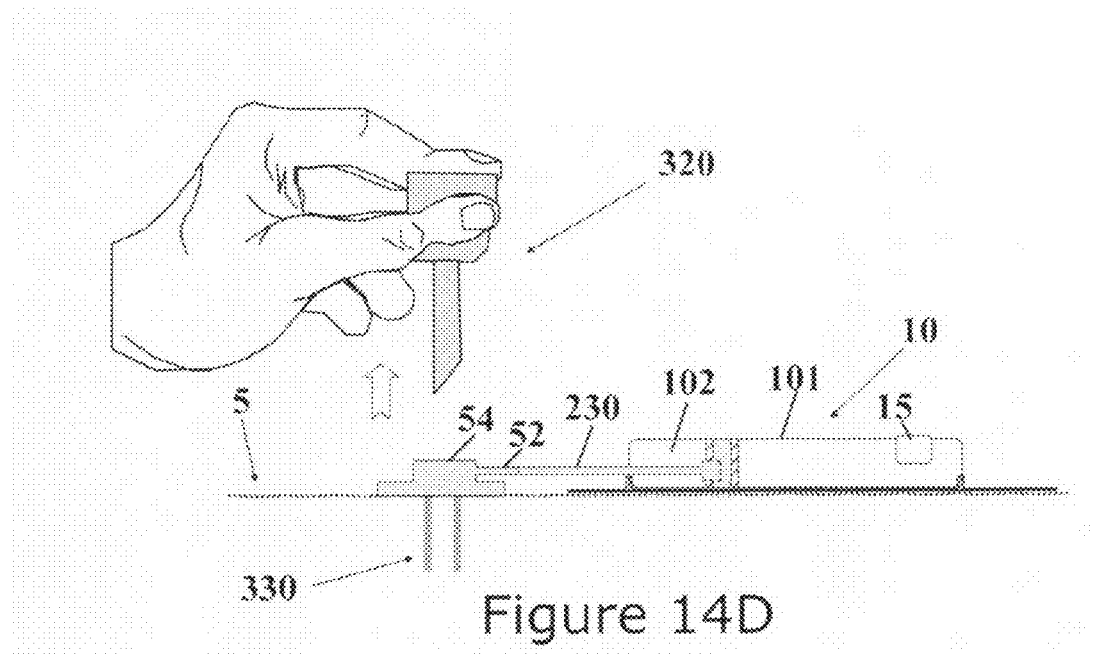

FIGS. 14A-D show an exemplary usage of an infusion set together with the dispensing patch unit (10), according to some embodiments of the present invention. FIG. 14A shows the dispensing patch unit (10). The delivery tube (230) extends from the dispensing patch unit (10) to an insertion site on the body of the patient (not shown in FIG. 14A). In the embodiment shown in FIGS. 14A-D, the insertion site can be located outside the area of the skin which is covered by the adhered carrier unit (30) (as shown in FIGS. 14B-D).

FIG. 14B shows the assembled dispensing patch unit (10) adhered to the skin (5) using a carrier unit (30). The delivery tube (230) protrudes away from the unit (10). FIG. 14B further illustrates an infusion set (50). The infusion set (50) includes a hub (54), a connecting tube (52), a cannula (330) and a penetrating member (320). The connecting tube (52) is coupled to the hub (54). The penetrating member (320) can include a needle or any other penetrating instrument (331) that pierces the skin of the patient at a desired location (i.e., the insertion site). As shown in FIG. 14B, penetrating member (320) along with the needle (331) are coupled to the hub (54) and the needle (331) is placed through the cannula (330) and protrudes away from the cannula (330).

FIG. 14c shows the dispensing patch unit (10) being adhered to the skin (5) of the patient and further connected to the infusion set (50). In some embodiments, the connecting tube (52) is coupled to the delivery tube (230) and then the needle (331) of the penetrating member (320) pierces the skin (5) at the insertion site and allows insertion of the cannula (330) with the needle (331) being disposed in the cannula (330), as illustrated in FIG. 14C. In some embodiments, the piercing of the skin may take place prior to connection of the tubes (52) and (320). By piercing the skin (5) of the patient, therapeutic fluid (e.g., insulin) can be delivered to the subcutaneous tissue of the patient via the delivery tube (230), through the connecting tube (52) and into the cannula (330).

Subsequent to the piercing of the skin (5), the penetrating member (320) is withdrawn from the hub (54) leaving the cannula (330) subcutaneously immersed beneath the skin (5), as illustrated in FIG. 14D. As stated above the cannula (330) is in fluid communication with the reservoir (220) located within the dispensing patch unit (10) via the tubes (52) and (230). In some embodiments, in order to further secure the hub (54) and the cannula (330), the hub (54) may have an adhesive strip on its bottom portion that allows adhering of the hub to the skin (5) once the skin is pierced by the penetrating member (320). Further, in some embodiments, the device (10) can become operational only upon detection of a connection of the tubes (52) and (230) and/or removal of the penetrating member (320) from the hub (54).

FIGS. 15A-17C illustrate exemplary embodiments of the invention showing connection of the reservoir (220) to the cannula (330) using a well-arrangement (60) and a penetrating cartridge (62). An example of such connection is disclosed in the commonly-owned patent applications U.S. Provisional Patent Application Ser. Nos. 60/833,110, filed Jul. 24, 2006, and 60/837,877, filed Aug. 14, 2006, and International Patent Application No. PCT/IL07/000932, filed Jul. 24, 2007, the disclosures of which are incorporated herein by reference in their entireties. The well-arrangement (60) allows the insertion site to be located underneath the dispensing unit (10) and/or the carrier unit (30) instead of being located outside, as illustrated in FIGS. 14A-D. The well-arrangement (60) further prevents accidental disconnections of the delivery tube (230) from the connecting tube of the infusion set (50), shown in FIGS. 14A-D.

Figure 15A:
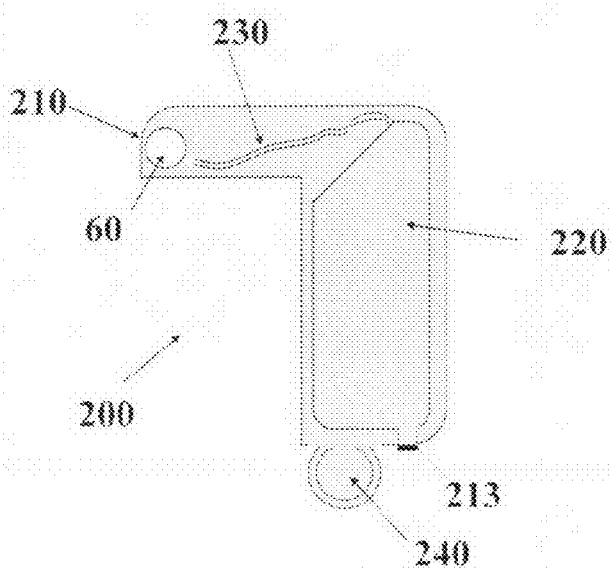
FIGS. 15A-C illustrate an exemplary dispensing patch unit provided with a well-arrangement, according to some embodiments of the present invention.

FIG. 15A shows an exemplary disposable part (200) that includes the battery (240), the reservoir (220) and the exit port (210). The exit port (210) includes the well-arrangement (60). The well-arrangement (60) is in fluid communication with the reservoir (220) via the delivery tube (230).

Figure 15B:
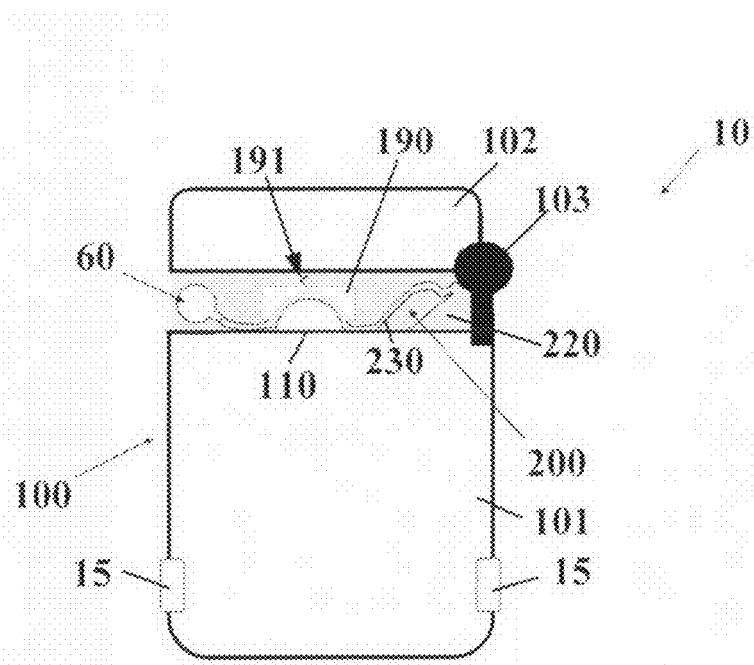

FIG. 15B shows the entire dispensing unit (10), wherein the reusable and disposable parts are coupled together and the cover portion (102) is being closed. The reservoir (220) is configured to supply therapeutic fluid to the well-arrangement (60) via the delivery tube (230) that is being squeezed by the rotary wheel (110) and the stator (190).

Figure 15C:
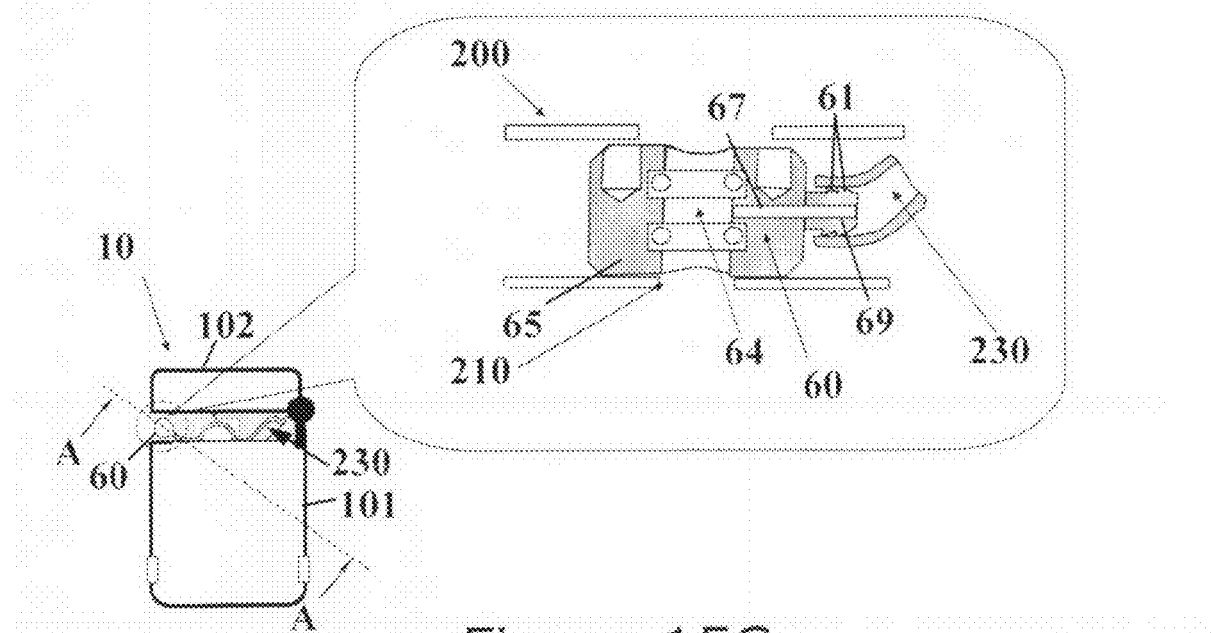

FIG. 15C is an enlarged cross-sectional view of the well-arrangement (60) taken along line A-A. The well-arrangement (60) includes a tube connector extension (69) that is connected to the delivery tube (230) using a snap-fit, Luer-lock, or any other type of connection. In some embodiments, the extension (69) includes a plurality of teeth (61) that prevent slippage of the tube (230) when the tube (230) is fitted over the extension (69), as shown in FIG. 15C. The well-arrangement (60) further includes a housing (65) that includes a bore (64). The bore (64) can be a closable channel that is in fluid communication with the delivery tube (230) when the tube (230) is fitted over the extension (69). Such fluid communication is provided by a channel (67) disposed within the housing (65). The bore (64) can have a cylindrical, square, oval, or any other suitable cross-section. The bore (64) further allows insertion of a penetrating cartridge including cannula or other devices carrying a cannula or any other fluid delivery device/channels. As illustrated in FIG. 15C, the well-arrangement (60) is in fluid communication with the exit port (210), through which a penetrating member carrying the cannula is inserted for delivery of the fluid to the patient.

Figure 16A:
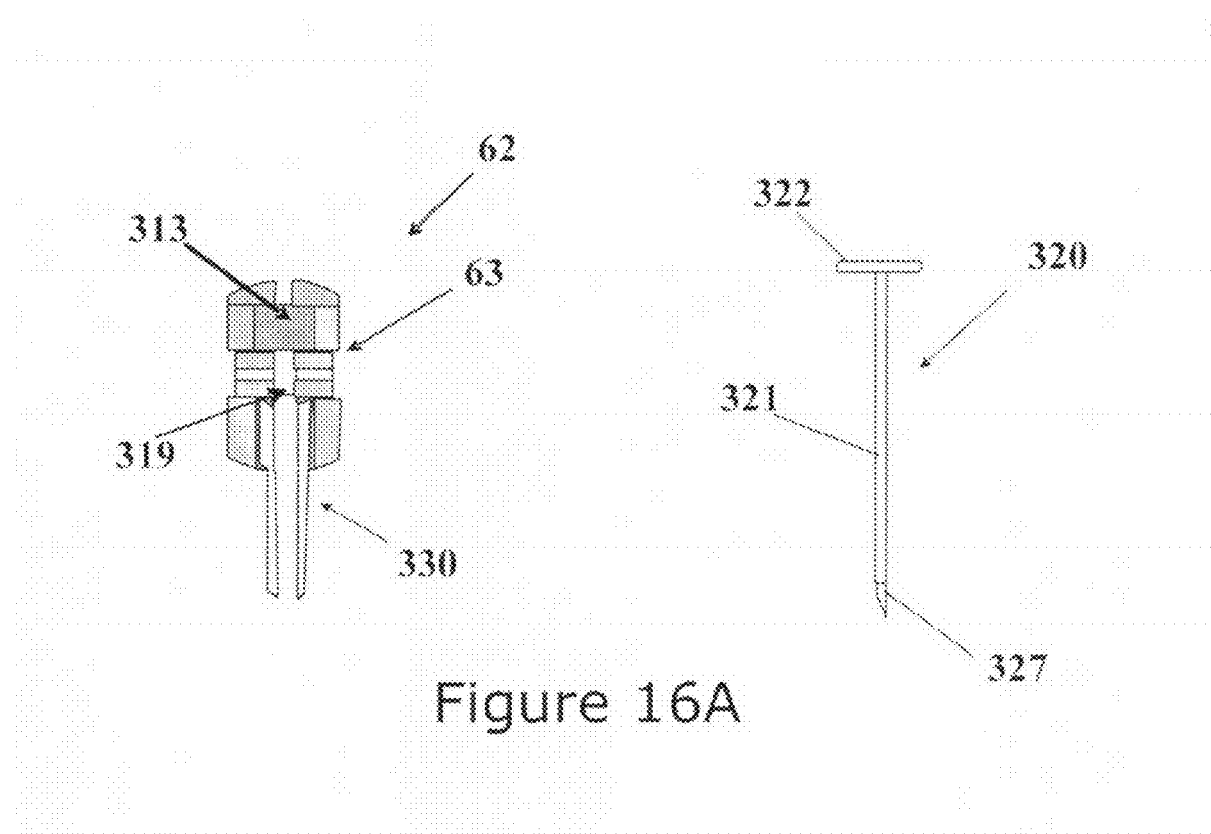
FIGS. 16A-B illustrate exemplary penetrating cartridge and penetrating member of the dispensing device, according to some embodiments of the present invention.
Figure 16B:
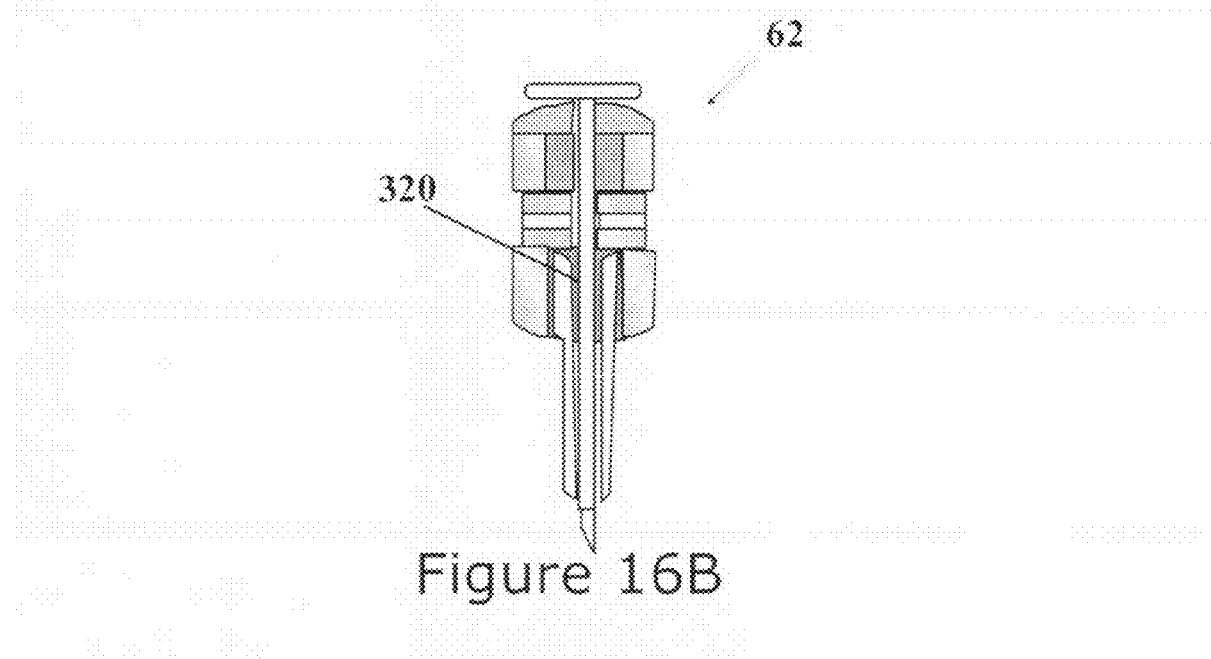

FIG. 16A shows the penetrating cartridge (62) having a body portion (63), the cannula (330), a self-sealable septum (313). The penetrating cartridge (62) further includes a channel (319) that extends from the top of the body portion (63) into the cannula (330). The channel (319) accommodates placement of a penetrating member (320) (shown on the right side of FIG. 16A). The self-sealable septum (313) is configured to seal the channel (319) when the penetrating member (320) is removed from the cartridge (62). The penetrating member (320) is composed of a dagger (321) having a sharp end (327) and a grip (322). The penetrating member (320) is adapted to pierce the surface of the skin (5). FIG. 16B shows the penetrating member (320) inserted into the penetrating cartridge (62).

Figure 17A:
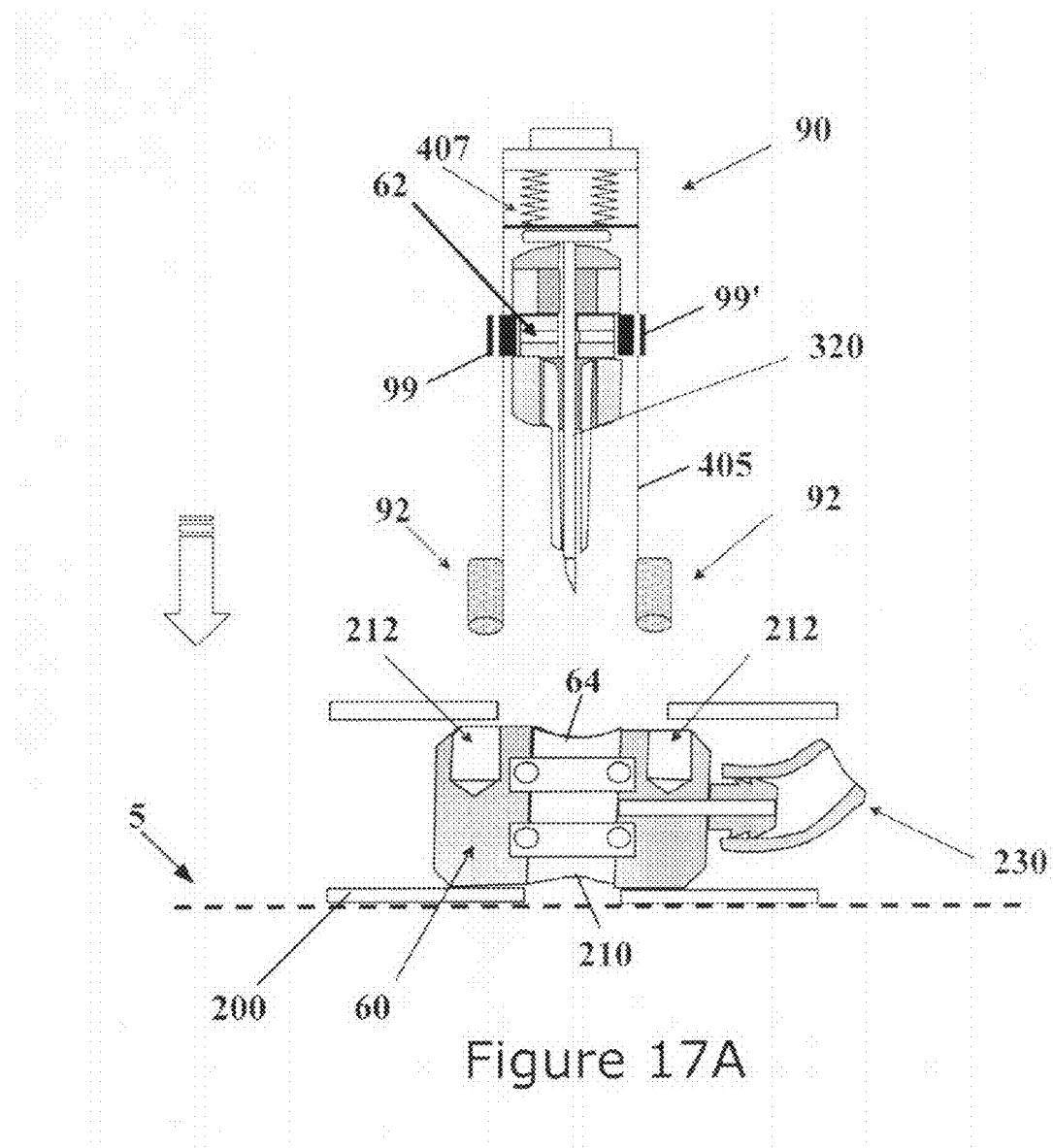
FIGS. 17A-C illustrate an exemplary penetrating cartridge (including cannula) insertion into the well arrangement using an inserter, according to some embodiments of the present invention.
Figure 17B:
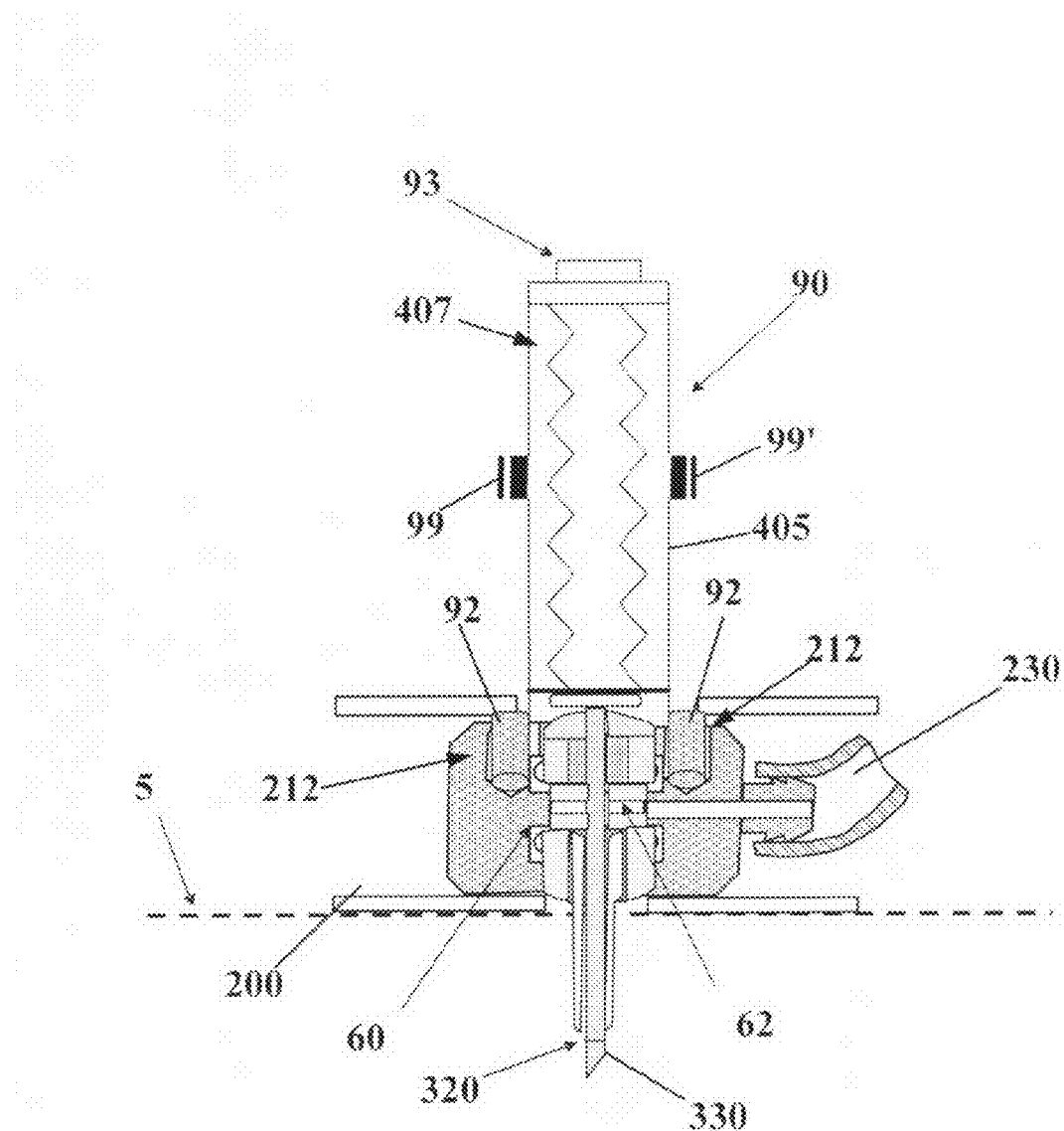
Figure 17C:
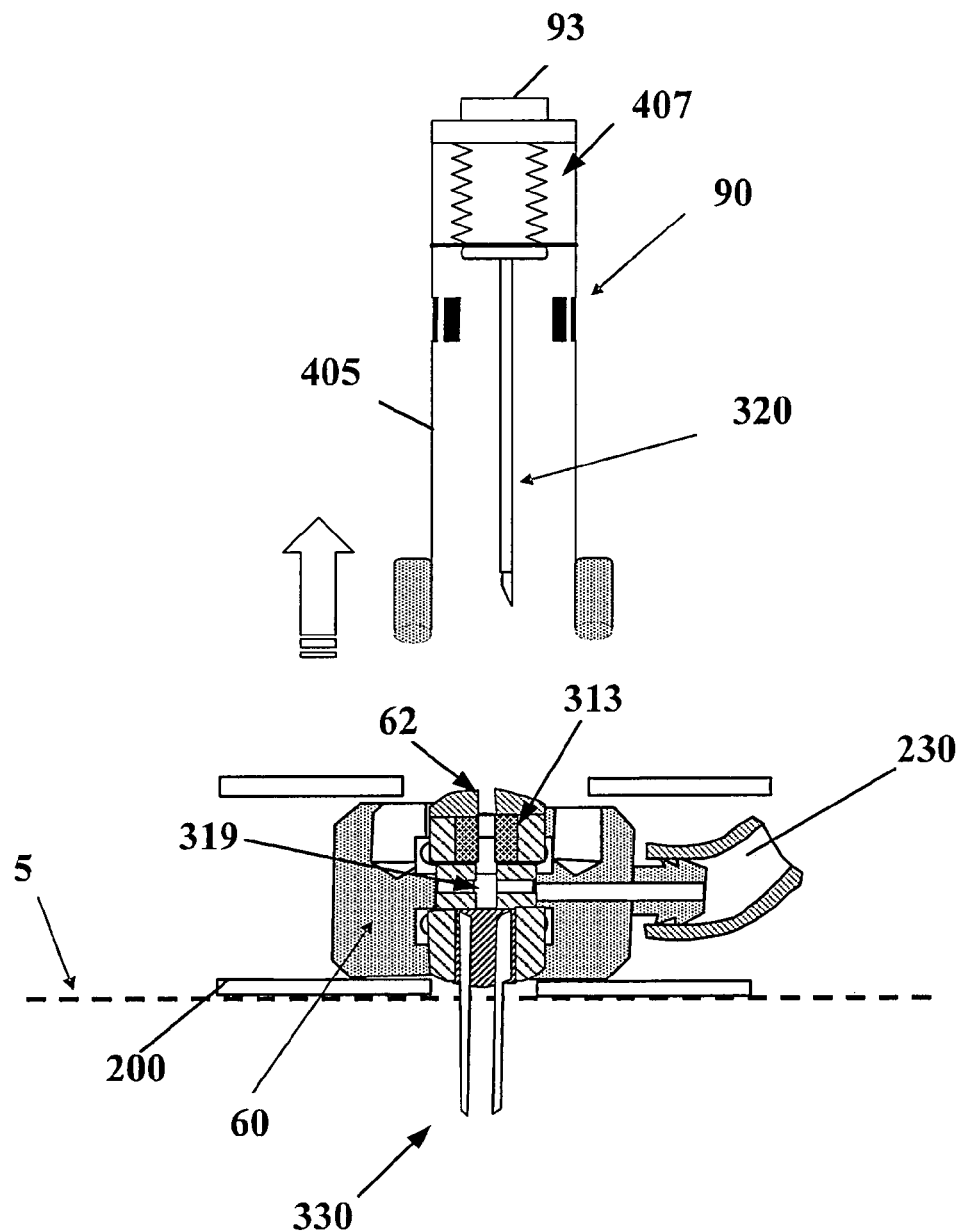

FIGS. 17A-C show insertion and subcutaneous placement of the cannula (330) into the body of the patient. In some embodiments, the insertion and subcutaneous placement of the cannula (330) can be performed using an insertion device, also referred-to as an inserter.

FIG. 17A is a cross-sectional view of an exemplary inserter (90), according to some embodiments of the present invention. The inserter (90) includes a hollow housing (405) that accommodates placement/loading of the penetrating member (320). The housing (405) further includes a releasable spring (407) that interacts with the housing (405) to release the penetrating member (320) into the well-arrangement (60) and stopper mechanism, for example constraints (99 and 99') that prevents slippage/misfiring of the penetrating member (320). The housing (405) further includes projections (92) that interact with corresponding recesses (212) created in the well-arrangement (60). The interaction between projections (92) and recesses (212) further secures the housing (405) that is loaded with the penetrating member (320) to the housing of the well-arrangement (60). This allows more precise insertion of the penetrating member (320) and the cannula (330) to the insertion site, as illustrated in FIG. 17B. An exemplary configuration and operation of the inserter (90) is disclosed in the commonly owned U.S. Provisional Patent Application Ser. No. 60/861,345, filed Nov. 28, 2006, and International Patent Application No. PCT/IL07/001454, filed Nov. 26, 2007, the disclosures of which are incorporated herein by reference in their entireties. As further illustrated in FIG. 17A, the delivery tube (230) can be coupled to the well-arrangement (60) prior to insertion of the penetrating member (320). In some embodiments, such coupling can take place after insertion of the penetrating member (320).

FIG. 17B shows cannula (330) being inserted into the subcutaneous tissue. Such insertion is accomplished by securing the housing (405) that is loaded with the penetrating member (320) to the housing of the well-arrangement (60) (using projections (92) and recesses (212)) and then releasing the spring (407), which pushes/fires the penetrating member (320) in a downward direction with regard to the surface of the skin (5). Upon being pushed, the penetrating member's (320) penetrating dagger (321) along with the cannula (330) pierce the skin (5) and enter the subcutaneous tissue of the patient. The spring (407) release is accomplished using a button (93) disposed at the top of the housing (405), which removes the constraints (99 and 99') allowing the releasing of the spring (407) and thus the firing of the penetrating member (320). Once the cannula (330) is inserted into the subcutaneous tissue, the penetrating member (320) along with the housing (405) can be removed, as illustrated in FIG. 17C. In some embodiments, upon depression of the button (93), the spring 407 compresses within the housing 405 thereby pulling the penetrating member (320) (which can be secured to the spring (407)) in an upward direction and the constraints (99 and 99') retain the penetrating member (320) within housing (405). In some embodiments, the removal of the penetrating member (320) can be done manually by pulling the housing (405) in an upward direction. Upon removal of the penetrating member (320), the self-sealing septum (313) seals the channel (319), thus, preventing any fluid leakage and/or contamination. Further, once the penetrating member (320) is removed, the cannula (330) remains in the subcutaneous compartment. The insertion of the penetrating member (320)/cannula (330) into the insertion site can be done at any desired angle.

FIGS. 18A-21C illustrate exemplary embodiments of the invention where the connection of the dispensing patch unit (10) to the skin (5) is done using a cradle unit. An example of the cradle unit is disclosed in a commonly-owned U.S. Provisional Patent Application Ser. No. 60/876,679, filed Dec. 22, 2006, U.S. patent application Ser. No. 11/963,481, filed Dec. 21, 2007, and International Patent Application No. PCT/IL07/001579, filed Dec. 20, 2007, the disclosures of which are incorporated herein by reference in their entireties.

In some embodiments, the cradle unit includes two parts as follows:
1. The cradle unit provided with
    a. a cradle base.
2. The penetrating cartridge unit having:
    a. a well portion;
    b. a cannula; and,
    c. a penetrating member.

Figure 18A:
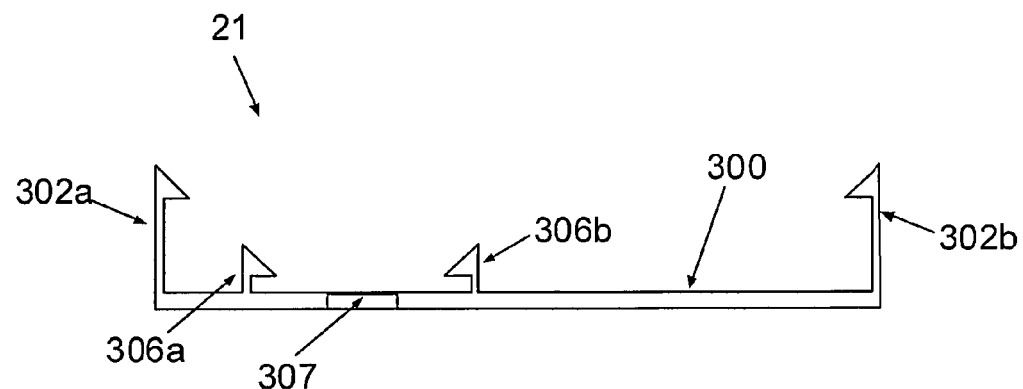
FIGS. 18A-D illustrate exemplary cradle unit and penetrating cartridge unit, according to some embodiments of the present invention.

FIGS. 18A-D show an exemplary cradle unit, according to some embodiments of the present invention. FIG. 18A shows the cradle part (21) that includes a cradle base (300), connecting latches (306(a, b, c)); an opening (307), and anchoring latches (302(a, b, c, d)) for connecting to the dispensing patch unit (10). FIG. 18A is a side view of the cradle part (21) and, thus, displays only two connecting latches (306) and two anchoring latches (302). The latches (302) and (306) are designed to have snap-on arrangement, whereby once the unit (10) is inserted into the cradle part (21), the latches (302) and (306) securely lock the unit (10) and/or its components to the base (300).

Figure 18B:
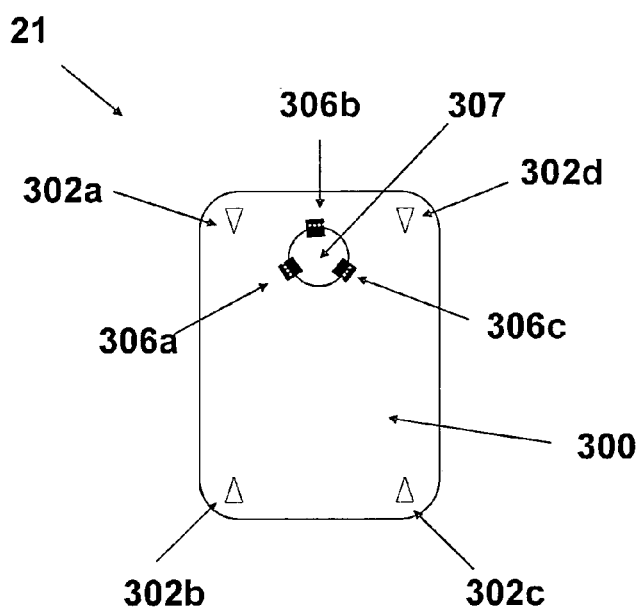
Figure 18C:
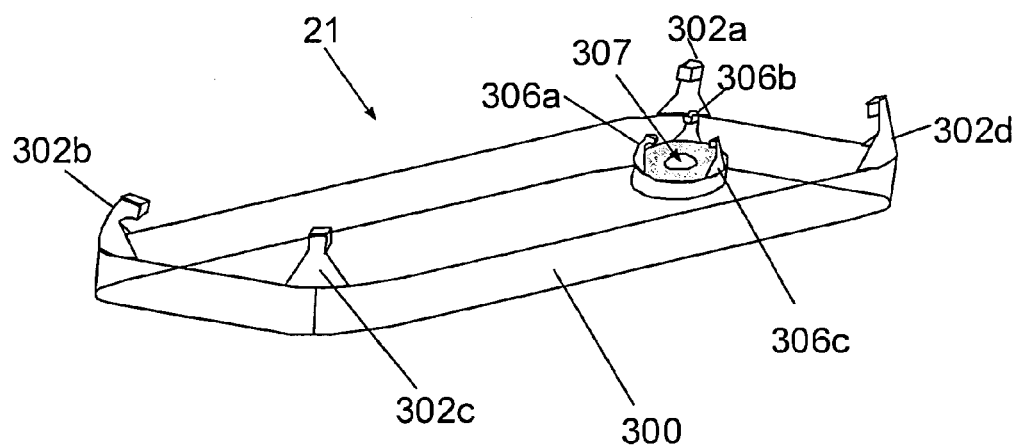

FIG. 18B-C are upper and isometric views, respectively, of the cradle part (21) including cradle base (300) and three connecting latches (306) disposed around the opening (307). The opening (307) and the latches (306) are configured to receive a cannula cartridge unit (22) shown in FIG. 18D.

Figure 18D:
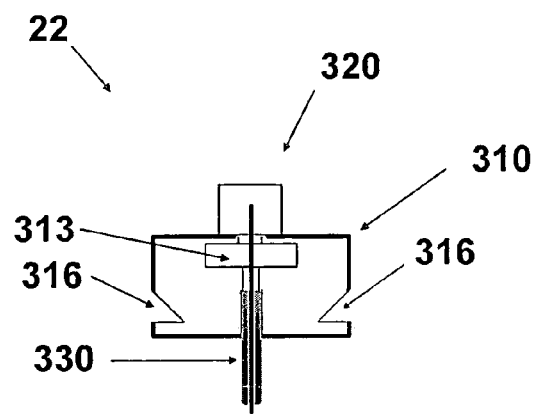

Referring to FIG. 18D, the cannula cartridge unit (22) includes a well portion (310), lateral recesses (316), a septum (313), the cannula (330) and the penetrating member (320). The lateral recesses (316) are configured to mate with latches (306) and create a snap-fit arrangement, which secures or anchors the cannula cartridge unit (22) to the opening (307). At the time of insertion of the cannula cartridge unit (22), the penetrating member (320) pierces the skin (5) (not shown in FIGS. 18A-D) and allows insertion of the cannula (330), as discussed above. Since, the latches (306) and the recesses (316) anchor the cannula cartridge unit (22), the penetrating member (320) can be removed while retaining the cannula (330) inserted into the subcutaneous tissue. The septum (313) seals the top portion of the passageway through which the penetrating member (320) is removed, as discussed above. The cannula cartridge unit (22) is shaped to allow substantially precise fit between the latches (306) and alignment of the cannula (330) along with the penetrating member (320) and the opening (307).

Figure 19A:
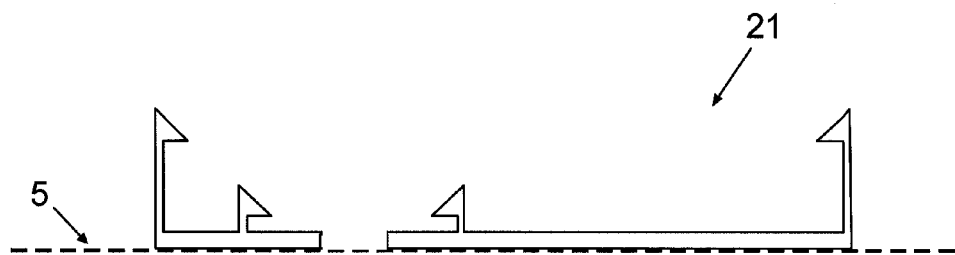
FIGS. 19A-D illustrate exemplary cross-sectional views of the cradle unit and penetrating cartridge unit and their connection, according to some embodiments of the present invention.
Figure 19B:
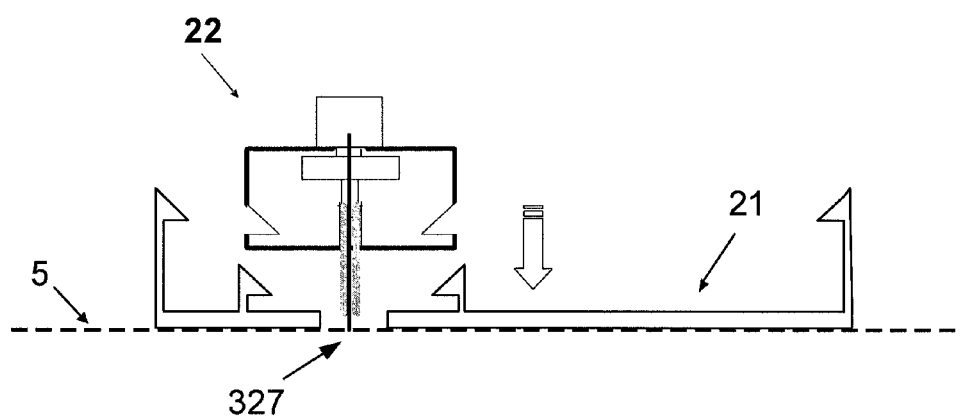
Figure 19C:
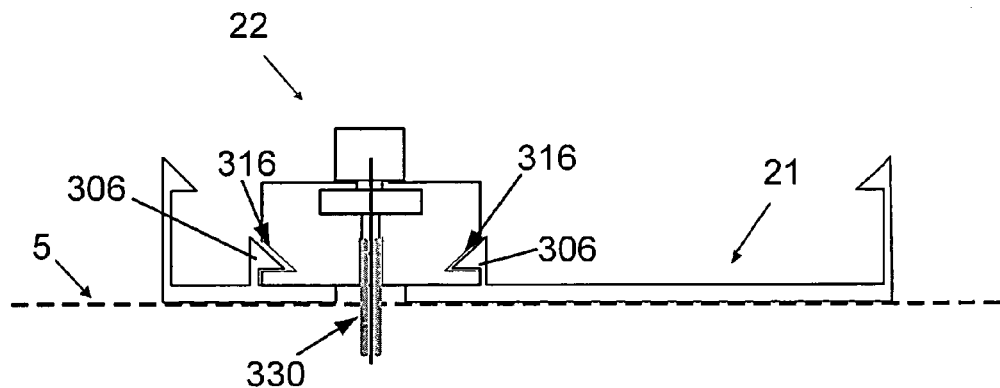
Figure 19D:
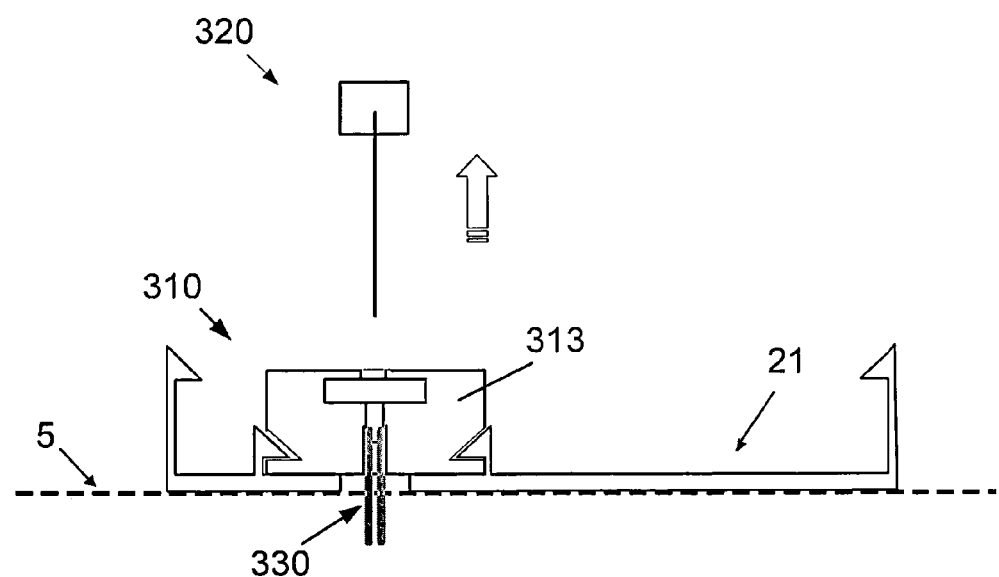

FIGS. 19A-D shows connection of the cradle part (21) and the cannula cartridge unit (22), as discussed above with regard to FIGS. 18A-D. FIG. 19A shows the cradle part (21) attached to the patient skin (5). The attachment can be done using adhesives or using any other means. As can be understood by one skilled in the art, the adhesive layer can be disposed on the side of the cradle base (300) that faces the skin (5). FIG. 19B shows the connection of the cannula cartridge unit (22) to the cradle part (21) using the latches (306) and the recesses (316). The sharp tip (327) of the penetrating member (320) pierces the skin (5) and leads the cannula (330) into the body of the patient. FIG. 19C shows the cannula cartridge unit (22) connected to the cradle part (21). FIG. 19D shows the removal of the penetrating member (320) from the cannula cartridge unit (22). The cradle part (21) is adhered to the skin (5) and the cannula (330) remains in the body. The self-sealable septum (313) of the well (310) allows repeated connection/disconnection with the connecting lumen (250) of the dispensing patch unit (10). The self-sealable septum (313) also prevents leaking and entrance of contaminants.

Figure 20A:
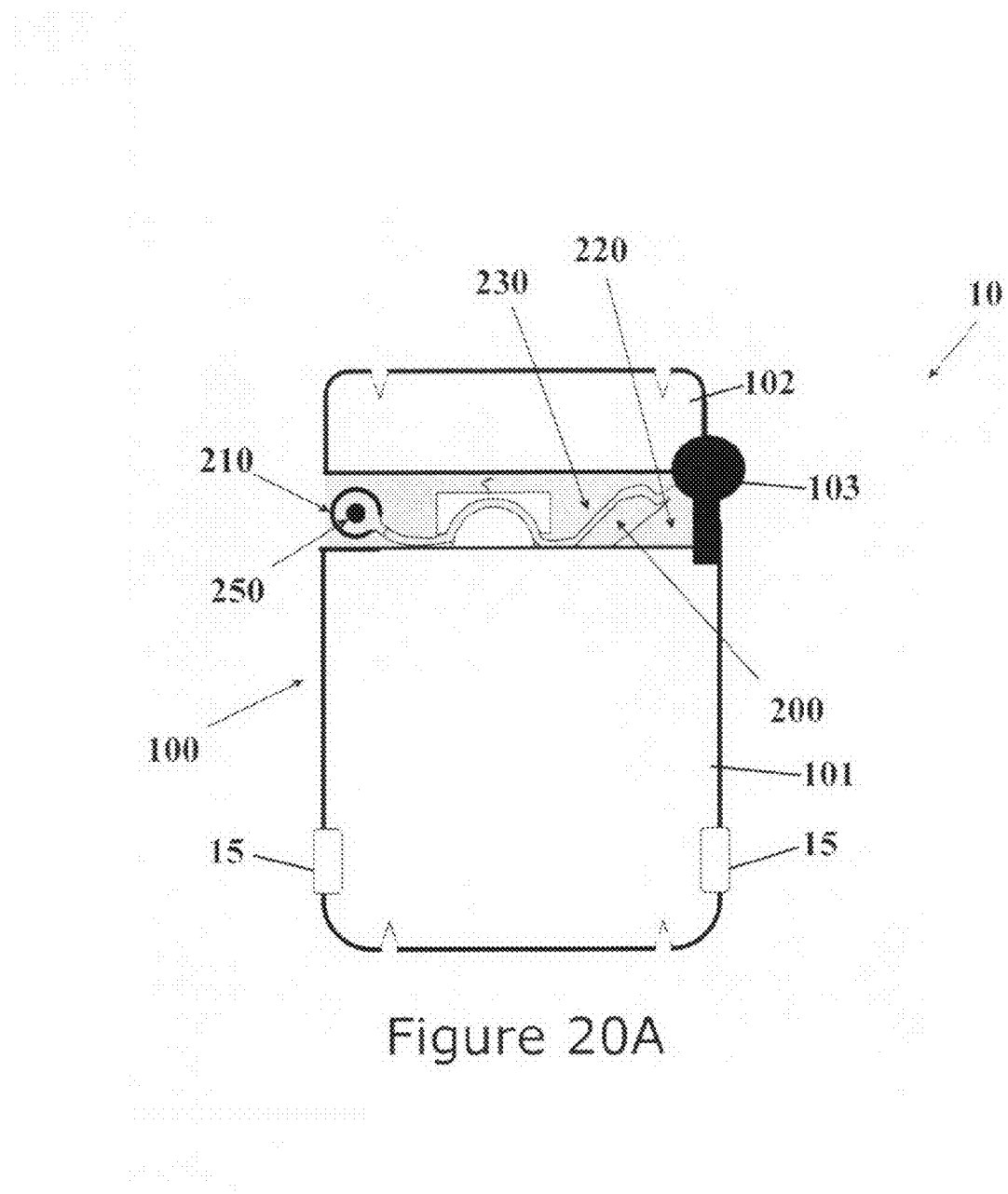
FIGS. 20A-B illustrate an exemplary dispensing patch unit with an exit port having a connecting lumen, according to some embodiments of the present invention.

FIGS. 20A-21C show connection and disconnection of the dispensing patch unit (10) to and from the cradle unit (21). FIG. 20A is a top view of the dispensing patch unit (10) including the reusable part (100) and the disposable part (200) and being coupled to the cradle unit (21). FIG. 20A further illustrates that the disposable part (200) includes the exit port (210), a connecting lumen (250), the delivery tube (230) and the reservoir (220). The connecting lumen (250) is disposed at the exit port (210). The delivery tube (230) is connected to the connecting lumen (250) that provides fluid communication between the reservoir (220), the delivery tube (230) and the cannula (330) (not shown in FIG. 20A).

Figure 20B:
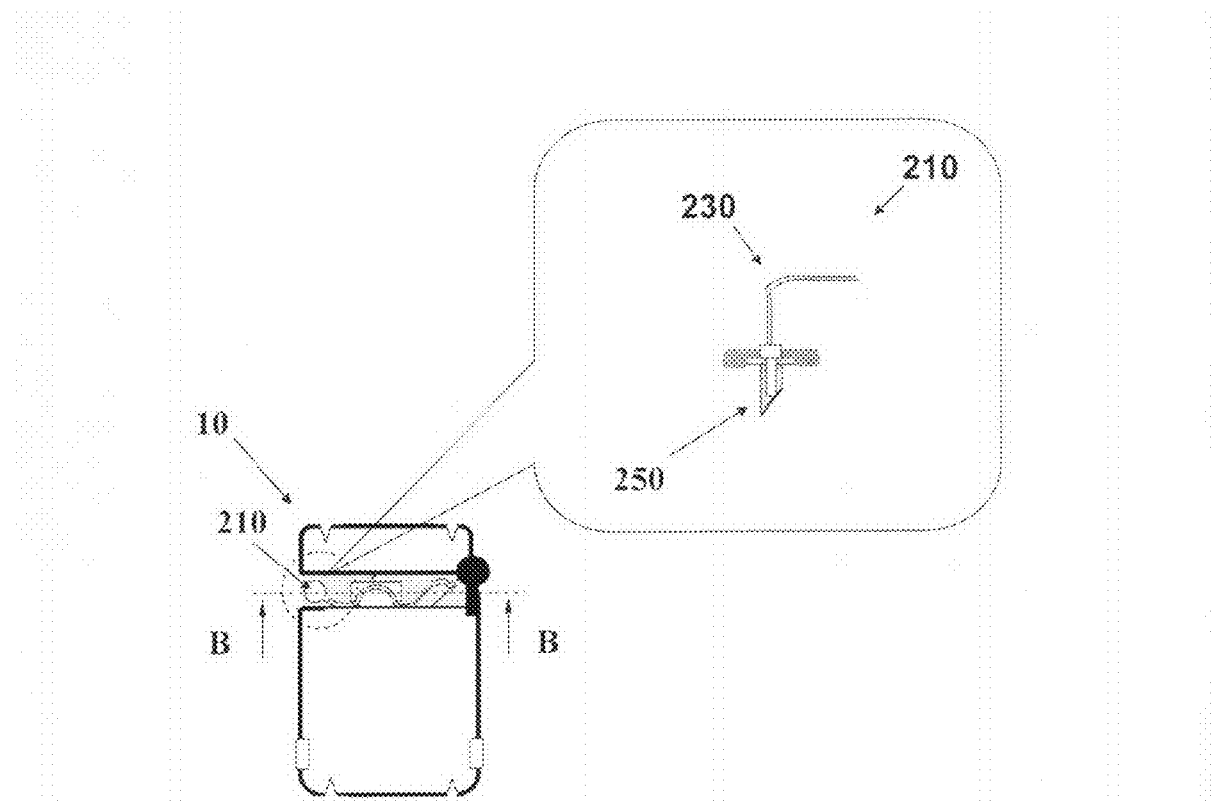

FIG. 20b further illustrates the detail of the connecting lumen (250) being rigidly connected to the delivery tube (230). The detailed cross-sectional view of the lumen (250) is shown along line B-B.

Figure 21A:
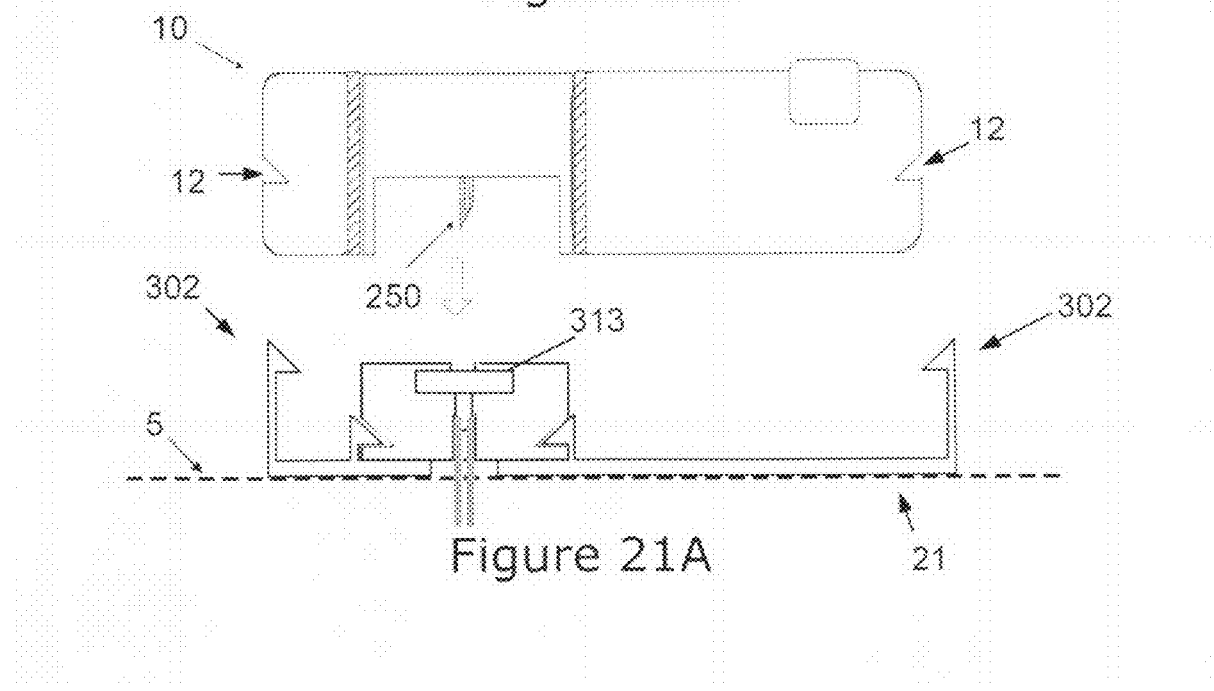
FIGS. 21A-C illustrate exemplary cross-sectional views of the connection and disconnection of the dispensing patch unit to and from the cradle unit, according to some embodiments of the present invention.

FIG. 21A shows connection of the dispensing patch unit (10) to the cradle unit (21). As stated above, the latches (302) are configured to secure the unit (10) to the cradle unit (21). The unit (10) further includes a plurality of lateral notches/recesses (12) that are configured to mate with the latches (302) upon placement of the unit (10) into the cradle unit (21). When the dispensing unit (10) is brought in close proximity to the cradle unit (21), the connecting lumen (250) pierces the well's self-sealing septum (313) allowing fluid communication between the cannula (330) and the reservoir (220).

Figure 21B:
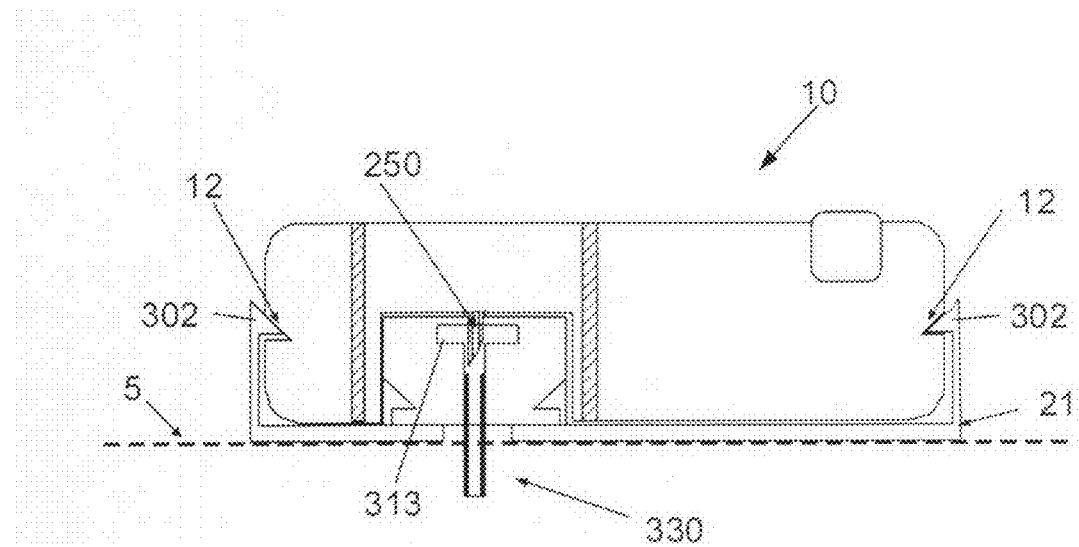

FIG. 21b shows the dispensing unit (10) being attached to the cradle unit (21) (i.e., the dispensing unit (10) being in operating mode). When the two units are connected the connecting lumen (250) pierces the septum (313) of the cradle unit (20) and enters in the cannula (330) maintaining fluid communication between reservoir (220) and cannula (330). The lateral notches (12) allow connecting of the dispensing patch unit (10) to the cradle unit (20) by anchoring latches (302).

Figure 21C:
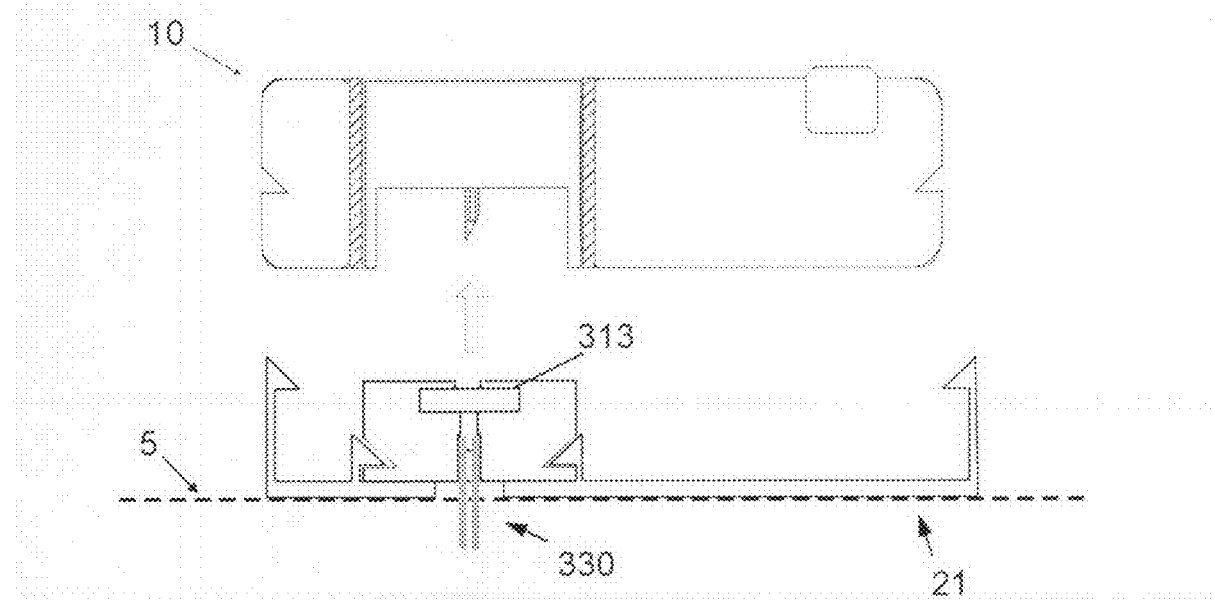

FIG. 21c shows disconnection of the dispensing patch unit (10). The elastically deformable latches (302) are pulled away from the unit's (10) housing and the unit (10) is released from the grip of the cradle unit (21). The cradle unit (21) remains adhered to the skin (5) and the cannula (330) also remains in the body. The self-sealable septum (313) avoids body fluids leaking and contamination.

In some embodiments, the dispensing patch unit can further include a sensing means (not shown) to measure and monitor body analyte(s) e.g., glucose sensor or continuous glucose monitor ("CGM"). In some embodiments, a dispensing patch unit and sensing means (also referred to as "dispensing system") can be capable of operating in one or more of a closed loop, open loop, or a semi-open loop mode. An example of such dispensing patch unit with the incorporated sensing means is disclosed in the commonly owned U.S. patent application Ser. No. 11/706,606, filed Feb. 14, 2007, and U.S. patent application Ser. No. 11/963,481, filed Dec. 21, 2007, the disclosures of which are incorporated herein by reference in their entireties.

In a closed loop mode, an analyte concentration is sensed by a sensor and determined by a processor and the processor commands a dispensing apparatus to dispense one or more therapeutic fluids to the human body based on the determined concentration. In an open loop mode, the sensing and dispensing functions are not linked. A device/system which operates in this mode could indicate a value for the determined analyte concentration, but no feedback control is exercised over the rate of dispensing. A user interface or other means by which a user can communicate commands to the device can allow the user to dispense the therapeutic fluid. In the semi-closed mode, the sensing occurs as noted above for the closed loop mode. However, the device/system can wait for confirmation/action or alternatively it can request such confirmation/action, possibly via some user interface, from a user before dispensing the therapeutic fluid in the amounts that might be needed based on the determined analyte concentration.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, presently unclaimed inventions are also contemplated. The inventors reserve the right to pursue such inventions in later claims.

All of the patents and pending patent applications referenced in this application are hereby incorporated by reference herein in their entireties.

What is claimed is:

1. An apparatus for delivering fluid to a mammal's body, comprising:
   a reusable part comprising:
      a reusable housing including a first portion and a second portion;
      a first part of a pump contained within the first portion of the reusable housing, wherein the first part comprises a stator stpported by a spring;
      a second part of the pump contained within the second portion of the reusable housing, wherein the second part of the pump comprises a rotary wheel with rollers; and
   a disposable part removably insertable into the reusable housing, the disposable part comprising at least a reservoir containing the fluid, and a fluid delivery tube;
   wherein the first portion of the reusable housing and the second portion of the reusable housing are configured together in a hinged arrangement for relative pivoting displacement between an open position in which the pump is disabled and a closed position in which, when the disposable part is inserted within the reusable housing, the pump is enabled, and
   wherein upon insertion of the disposable part into the housing, and relative displacement of the first portion and the second portion from the open position to the closed position, at least portion of the delivery tube is pressed against the rotary wheel by the stator thereby effecting peristaltic pumping.

2. The apparatus of claim 1, wherein the pump comprises a linear positive displacement pump.

3. The apparatus of claim 1, wherein the second portion of the housing further contains the motor.

4. The apparatus of claim 1, wherein the disposable part comprises a cassette-like configuration.

5. The apparatus of claim 1, wherein at least a portion of the reservoir is transparent.

6. The apparatus of claim 1, wherein at least a portion of one or more of the first portion of the housing and the second portion of the housing is transparent.

7. The apparatus of claim 1, wherein the disposable part further comprises an exit port for connection to a cannula.

8. The apparatus of claim 1, wherein the disposable part further comprises a well arrangement.

9. The apparatus of claim 1, further comprising a seal for sealing the apparatus when the housing is in the closed position.

10. The apparatus of claim 9, wherein the seal comprises at least one gasket.

11. The apparatus of claim 1, wherein the housing is attachable to a carrier unit.

12. The apparatus of claim 11, wherein the apparatus further comprises the carrier unit, and wherein the disposable part and the carrier unit are unitary.

13. The apparatus of claim 1, wherein the housing is attachable to a cradle.

14. The apparatus of claim 13, wherein the cradle is adapted to receive a cannula cartridge unit.

15. The apparatus of claim 1, wherein at least one of the first portion of the housing and the second portion of the housing is adherable to the mammal's skin.

16. The apparatus of claim 1, further comprising a remote control.

17. The apparatus of claim 1, wherein at least one of the first portion of the housing and the second portion of the housing is provided with at least one control button.

18. The apparatus of claim 1, wherein
at least one of the first portion of the housing and the second portion of the housing further contains a printed circuit board and electrical contacts;
the disposable part comprises one or more batteries; and
upon insertion of the disposable part into the housing, the one or more batteries are connected to the printed circuit board using the electrical contacts.

19. The apparatus of claim 1, wherein the disposable part further comprises a filling port in fluid communication with the reservoir.

20. The apparatus of claim 1, wherein the disposable part is entirely contained within the reusable housing when inserted thereto.

21. The apparatus of claim 1, wherein the reservoir comprises the source of the fluid.

22. The apparatus of claim 1, wherein the disposable part further comprises a delivery tube for delivering the fluid from the reservoir toward an exit port of the disposable part.

23. The apparatus of claim 1, wherein the reusable part is configured for repetitive use via subsequent inserting and removing of one or more other disposable parts.

24. The apparatus of claim 1, wherein the at least one component is capable of being inserted into the housing and removed therefrom only when the housing is in the open position.

25. An apparatus for delivering fluid to a mammal's body, comprising:
first part of a pump contained within a first portion of a housing, wherein the first part comprises a stator supported by a spring;
a second part of the pump contained within a second portion of the housing, wherein the second part of the pump comprises a rotary wheel with rollers; and
at least one component, separate from the portions of the housing, configured for removable insertion into the housing so as to be entirely contained within the housing when inserted, the at least one component including a fluid delivery tube;
wherein:
the first portion of the housing and the second portion of the housing are configured together in a hinged arrangement for relative pivoting displacement between an open position and a closed position,
the at least one component is configured to operatively couple to the first and second parts of the pump upon inserting the at least one component into the housing and displacing the first and second portions of the housing from the open position to the closed position, and
upon insertion of the at least one component into the housing, and relative displacement of the first portion and the, second portion from the open position to the closed position, at least portion of the delivery tube is pressed against the rotary wheel by the stator thereby effecting peristaltic pumping.

26. An apparatus for delivering fluid to a mammal's body, comprising:
a first part of a pump contained within a first portion of a housing, wherein the first part comprises a stator supported by a spring;
a second part of the pump contained within a second portion of the housing, wherein the second part of the pump comprises a rotary wheel with rollers; and
at least one component, separate from the portions of the housing, configured for removable insertion within the housing, the at least one component including a reservoir and a fluid delivery tube;
wherein the first portion of the housing and the second portion of the housing are configured together in a hinged arrangement for relative pivoting displacement between an open position in which the at least one component can be removably inserted into the housing and a closed position in which the at least one component is captured by the portions of the housing; and
wherein upon insertion of the at least one component into the housing and relative displacement of the first portion and second portion to the closed position, at least a portion of the fluid delivery tube is pressed against the rotary wheel by the stator thereby effecting peristaltic pumping.

27. An apparatus for delivering fluid to a mammal's body, comprising:
a cover having provided therein a first part of a pump, wherein the first part comprises a stator supported by a spring;
a housing having provided therein a second part of the pump, wherein the second part of the pumpcomprises a rotary wheel with rollers; and
at least one stand-alone component, separate from the cover and the housing configured for removable insertion within the housing such that the at least one stand-alone component is entirely contained within the housing when inserted, wherein the stand alone corpponent includes a reservoir and a fluid delivery tube;
wherein the cover is configured for relative displacement with the housing between an open position in which the pump is disabled and a closed position in which, when the at least one stand-alone component is inserted within the housing, the pump is enabled; and
wherein upon insertion of the at least one stand-alone component and relative displacement of the cover and the housing from open position to the closed position, at least portion of the delivery tube is pressed against the rotary wheel by the stator thereby,effecting peristaltic pumping.

28. An assembly for delivery a fluid to a mammal's body, comprising:
a skin-adherent part comprising an adhesive for adhering to the mammal's body;

a fluid delivery part adapted to connect to the skin-adherent part; the fluid delivery part comprising:
- a cover having provided therein a first part of a pump, wherein the first part of the pump comprises a stator supported by a spring;
- a housing having provided therein a second part of the pump, wherein the second part of the pump comprises a rotary wheel with rollers; and
- at least one stand-alone component, separate from the cover and the housing configured for removable insertion within the housing such that the at least one stand-alone component is entirely contained within the housing when inserted;

wherein the cover is configured for relative displacement with the housing between an open position in which the pump is disabled and a closed position in which, when the at least one stand-alone component is inserted within the housing, the pump is enabled;

wherein the at least one stand-alone component comprises a reservoir for storing the source of the fluid, and a fluid delivery tube; and wherein upon insertion or of the one stand-alone component into the housing and relative displacement of the cover and the housing from the open position to the closed position, at least a portion of the delivery tube is pressed against the rotary wheel by the stator thereby effecting peristaltic pumping.

29. The assembly of claim 28, wherein the skin-adherent part is a cradle.

30. The assembly of claim 28, wherein the skin-adherent part is a carrier unit.

* * * * *